US006617422B1

(12) United States Patent
Nielsen et al.

(10) Patent No.: US 6,617,422 B1
(45) Date of Patent: *Sep. 9, 2003

(54) PEPTIDE NUCLEIC ACID MONOMERS AND OLIGOMERS

(75) Inventors: Peter E. Nielsen, Kokkedal (DK); Gerald Haaima, Toowong (AU); Anne B. Eldrup, Copenhagen (DK)

(73) Assignee: Peter Nielsen (DK)

( * ) Notice: Subject to any disclaimer, the term of this patent is extended or adjusted under 35 U.S.C. 154(b) by 0 days.

This patent is subject to a terminal disclaimer.

(21) Appl. No.: 08/862,629

(22) Filed: May 23, 1997

(51) Int. Cl.$^7$ ................................................. C07K 7/00
(52) U.S. Cl. ........................ 530/300; 435/6; 536/24.3; 536/24.31; 536/24.32; 536/23.1; 514/45; 514/49; 530/332; 530/323
(58) Field of Search ............................ 435/6; 536/24.3, 536/24.31, 24.32, 23.1; 514/45, 49; 530/332, 323, 300

(56) References Cited

U.S. PATENT DOCUMENTS

| | | | |
|---|---|---|---|
| 3,687,808 A | 8/1972 | Merigan, Jr. et al. | 435/91.3 |
| 5,502,177 A | 3/1996 | Matteucci et al. | 536/26.6 |
| 5,539,082 A | 7/1996 | Nielsen et al. | 530/300 |
| 5,539,083 A | 7/1996 | Cook et al. | 530/333 |
| 5,786,461 A | 7/1998 | Buchardt et al. | 536/18.7 |

FOREIGN PATENT DOCUMENTS

| | | |
|---|---|---|
| WO | WO 92/20702 | 11/1992 |
| WO | WO 92/20703 | 11/1992 |
| WO | WO 93/12129 | 6/1993 |
| WO | WO 93/25706 | 12/1993 |
| WO | WO 94/28171 | 12/1994 |
| WO | WO 95/01370 | 1/1995 |
| WO | WO 95/14708 | 6/1995 |
| WO | WO 95/14789 | 6/1995 |
| WO | WO 95/15974 | 6/1995 |
| WO | WO 95/16202 | 6/1995 |
| WO | WO 96/02558 | 2/1996 |
| WO | WO 97/32888 | 9/1997 |

OTHER PUBLICATIONS

Kitagawa (J Biochem [Tokyo] 102 (5), 1203–1212, 1987).*
Bhan, Purshotam (Nucleic Acids Research vol. 25, No. 16, pp. 3310–3317, 1997).*
Kohwi Y. (J. Mol. Biol. 223 (4), 817–822, 1992).*
Chastain M (Nucleic Acids Res 29 (2), 315–318, 1992).*
Gee J. E. (J. Biol. Chem. 267 (16), 11163–11167, 1992).*
Pilch, Daniel S. (Proceedings of the National Academy of Sciences vol. 91, No. 20, pp. 9332–9336, 1994).*
Xodo, Luigi E. (Journal of Biomolecular Structure & Dynamics vol. 11, No. 4, pp. 703–720, 1994).*
Hildbrand J Am Chem Soc 119, 5499, 1997.*
Wittung J Am Chem Soc 119, 3189, 1997.*
Luyten, Eur. J. Med. Chem. 33, 515–576, 1998.*
Ferrer, Bioorg. Med. Chem. 8, 291, 2000.*
Srinivasan, J Am Chem Soc 120, 492, 1998.*
Wittung, J. Am. Chem. Soc. 119, 3189, 1997.*
Best et al., "Energetics of Formation of Sixteen Triple Helical Complexes Which Vary at a Single Position within a Pyrimidine Motif", *J. Am. Chem. Soc.*, 1995, 117(4), 1187–1193.
Crooke and Lebleu (eds.), *Antisense Research and Application*, CRC Press, 1993, Chapter 15, 274–288.
Egholm et al., "PNA hybridizes to complementary oligonucleotides obeying the Watson–Crick hydrogen–bonding rules", *Nature,* 1993, 365, 566–568.
Egholm et al., "Peptide Nucleic Acids (PNA). Oligonucleotide Analogues with an Achiral Peptide Backbone", *J. Am. Chem. Soc.,* 1992, 114, 1895–1897.
Egholm et al., "Recognition of Guanine and Adenine in DNA by Cytosine and Thymine Containing Peptide Nucleic Acids (PNA)", *J. Am. Chem. Soc.,* 1992, 114, 9677–9678.
Greenberg et al., "Energetics of Formation of Sixteen Triple Helical Complexes Which Vary at a Single Position within a Purine Motif", *J. Am. Chem. Soc.,* 1995, 117, 5016–5022.
Hyrup et al., "Peptide Nucleic Acids (PNA): Synthesis, Properties and Potential Applications", *Bioorganic Med. Chem.,* 1996, 4(1), 5–23.
Knudsen et al., "Antisense properties of duplex– and triplex–forming PNAs", *Nucl. Acids Res.,* 1996, 24(3), 494–500.
Lin et al., "Tricyclic 2'–Deoxycytidine Analogs: Synthesis and Incorporation into Oligodeoxynucleotides Which Have Enhanced Binding to Complementary RNA", *J. Am. Chem.,* 1985, 117, 3873–3874.
Lehninger, "The amino acid building blocks of proteins", *Biochemistry,* Second Edition, Worth Publishers, Inc., 1975, Ch. 4, 73–77.
Matteucci et al., "Hydridization Properties of Oligonucleotides Bearing a Tricyclic 2'–Deoxycytidine Analog Based on a Carbazole Ring System", *Tetra. Lett.,* 1996, 37(29), 5057–5060.
Moser et al., "Sequence–Specific Cleavage of Double Helical DNA by Triple Helix Formation", *Science,* 1987, 238, 645–650.
Nielsen et al., "Strand Displacement Binding of a Duplex–Forming Homopurine PNA to a Homopyrimidine Duplex DNA Target", *J. Am. Chem. Soc.,* 1996, 118, 2287–2288.
Nielsen et al., "Sequence–Selective Recognition of DNA by Strand Displacement with a Thymine–Substituted Polyamide", *Science,* 1991, 254, 1497–1500.

(List continued on next page.)

*Primary Examiner*—Christopher S. F. Low
*Assistant Examiner*—David Lukton
(74) *Attorney, Agent, or Firm*—Woodcock Washburn LLP

(57) ABSTRACT

Novel peptide nucleic acid (PNA) oligomers and their constituent monomers are disclosed. The PNA oligomers and linked PNAs form triple stranded structures with nucleic acids that show an increased specificity for thymidine in nucleic acid targets relative to naturally occurring nucleobases.

41 Claims, No Drawings

OTHER PUBLICATIONS

Nielsen, "Peptide nucleic acid (PNA): A lead for gene therapeutic drugs", Trainor (ed.), *Perspective Drug Disc. Des.,* 1996, 4, 76–84.

Patel, "Marriage of convience", *Nature,* 1993, 365, 490–492.

Shanmugam, "Another Approach to the Synthesis of Furo(2, 3–b) quinolines", *Naturforsh,* 1973, 196, 551–553.

Uhlmann et al., "Antisense Oligonucleotides: A New Therapeutic Principle", *Chem. Rev.,* 1990, 90(4), 544–584.

Eldrup, A.B., et al., "A novel peptide nucleic acid monomer for recognition of thymine in triple–helix structures," *J. Am. Chem. Soc.,* 1997, XP–002199522, 119, 11116–11117.

Nielsen, P.E., et al., "Sequence–specific transcription arrest by peptide nucleic acid bound to the DNA template strand," *Elsevier Science B. V.,* 1994, XP 002022886, 149, 1994, 139–145.

* cited by examiner

PEPTIDE NUCLEIC ACID MONOMERS AND OLIGOMERS

FIELD OF THE INVENTION

The present invention is directed to oligomeric compounds and their constituent monomers, especially peptide nucleic acid (PNA) oligomers and monomers. The peptide nucleic acid oligomers are useful for forming-triple helix (triplex) structures with nucleic acids with increased binding specificity. In one aspect of the present invention novel PNA oligomers have increased specificity for thymidine and deoxyuridine in triplex structures.

BACKGROUND OF THE INVENTION

Peptide nucleic acids are useful surrogates for oligonucleotides in binding to both DNA and RNA. See Egholm et al., Nature, 1993, 365, 566–568 and references cited therein).

PNA binds both DNA and RNA to form PNA/DNA or PNA/RNA duplexes. The resulting PNA/DNA or PNA/RNA duplexes are bound with greater affinity than corresponding DNA/DNA or DNA/RNA duplexes as evidence by their higher melting temperatures (Tm). This high thermal stability has been attributed to the neutrality of the PNA backbone, which does not encounter the charge repulsion present in DNA or RNA duplexes. The neutral backbone of the PNA also renders the Tms of PNA/DNA(RNA) duplexes practically independent of salt concentration. Thus the PNA/DNA duplex offers a further advantage over DNA/DNA duplex interactions which are highly dependent on ionic strength. Homopyrimidine PNAs have been shown to bind complementary DNA or RNA forming $(PNA)_2$/DNA-(RNA) triplexes of high thermal stability (see, e.g., Nielsen, et al., Science, 1991, 254, 1497; Egholm, et al., J. Am. Chem. Soc., 1992, 114, 1895; Egholm, et al., J. Am. Chem. Soc., 1992, 114, 9677).

In addition to increased affinity, PNA has also been shown to bind to DNA with increased specificity. When a PNA/DNA duplex mismatch is melted relative to the DNA/DNA duplex there is seen an 8 to 20° C. drop in the Tm. This magnitude of a drop in Tm is not seen with the corresponding DNA/DNA duplex with a mismatch present. See Egholm, M., et al., Nature 1993 365 p. 566.

The binding of a PNA strand to a DNA or RNA strand can occur in one of two orientations. The orientation is said to be anti-parallel when the DNA or RNA strand in a 5' to 3' orientation binds to the complementary PNA strand such that the carboxyl end of the PNA is directed towards the 5' end of the DNA or RNA and amino end of the PNA is directed towards the 3' end of the DNA or RNA. In the parallel orientation the carboxyl end and amino end of the PNA are in reverse orientation with respect to the 5'-3' direction of the DNA or RNA.

Because of their properties, PNAs are known to be useful in several different applications. In particular, PNAs have been used to form duplexes and triplexes with complementary RNA or DNA (see e.g., Knudsen et al., Nucleic Acids Res., 1996, 24, 494–500; and Nielsen et al., J. Am. Chem. Soc., 1996, 118, 2287–2288). Additionally, several review articles have recently been published in this area. See e.g., Hyrup et al., Bioorganic & Med. Chem., 1996, 4, 5–23; Nielsen, "Peptide nucleic acid (PNA): A lead for gene therapeutic drugs," in Trainor (Ed.), Perspectives Drug Disc. Des., 1996, 4, 76–84.

Since PNAs have stronger binding and greater specificity than oligonucleotides, they are of great utility as probes in cloning, blotting procedures, and in applications such as fluorescence in situ hybridization (FISH). Homopyrimidine PNAs are used for strand displacement in homopurine targets. The local triplex inhibits gene transcription. Additionally, the restriction sites that overlap with or are adjacent to the D-loop will not be cleaved by restriction enzymes. The binding of PNAs to specific restriction sites within a DNA fragment can inhibit cleavage at those sites. Such inhibition is useful in cloning and subcloning procedures. Labeled PNAs are also used to directly map DNA molecules by hybridizing PNA molecules having a fluorescent or other type of detectable label to complementary sequences in duplex DNA using strand invasion.

PNAs also have been used to detect point mutations in PCR-based assays (PCR clamping). In PCR clamping, PNA is used to detect point mutations in a PCR-based assay, e.g. the distinction between a common wild type allele and a mutant allele, in a segment of DNA under investigation. Typically, a PNA oligomer complementary to the wild type sequence is synthesized and included in the PCR reaction mixture with two DNA primers, one of which is complementary to the mutant sequence. The wild type PNA oligomer and the DNA primer compete for hybridization to the target. Hybridization of the DNA primer and subsequent amplification will only occur if the target is a mutant allele. With this method, the presence and exact identity of a mutant can be determined.

Considerable research is being directed to the application of oligonucleotides and oligonucleotide analogs that bind complementary DNA and RNA strands for use as diagnostics, research reagents and potential therapeutics. For many uses, the oligonucleotides and oligonucleotide analogs must be transported across cell membranes or taken up by cells to express activity.

PCT/EP/01219 describes novel peptide nucleic acid (PNA) compounds which bind complementary DNA and RNA more tightly than the corresponding DNA. It is desirable to append to these compounds groups which modulate or otherwise influence their activity or their membrane or cellular transport. One method for increasing such transport is by the attachment of a pendant lipophilic group.

The synthesis of peptide nucleic acids via preformed monomers has been described in International patent applications WO 92/20702 and WO 92/20703, the contents of each of which are incorporated herein by reference in their entirety. Recent advances have also been reported on the synthesis, structure, biological properties, and uses of PNAs. See for example WO 93/12129 and U.S. Pat. No. 5,539,083 to Cook et al., Egholm et al., Nature, 1993, 365, 566–568, Nielsen et al., Science, 1991, 254, 1497–1500; and Egholm et al., J. Am. Chem. Soc., 1992, 114, 1895–1897. Peptide nucleic acids also have been demonstrated to effect strand displacement of double stranded DNA (see Patel, D. J., Nature, 1993, 365, 490–492). The contents of each of the foregoing patents and publications are incorporated herein by reference in their entirety.

Triple helix formation by oligonucleotides has been an area of intense investigation since sequence-specific cleavage of double-stranded deoxyribonucleic acid (DNA) was demonstrated by Moser et al., Science, 1987, 238, 645–650. Triplex-forming oligonucleotides are believed to be of potential use in gene therapy, diagnostic probing, and other biomedical applications. See e.g., Uhlmann et al., Chemical Reviews, 1990, 90, 543–584.

Pyrimidine oligonucleotides have been shown to form triple helix structures through binding to homopurine targets in double-stranded DNA. In these structures the new pyrimidine strand is oriented parallel to the purine Watson-Crick strand in the major groove of the DNA, and binds through sequence-specific Hoogsteen hydrogen bonds. The sequence-specificity is derived from thymine recognizing adenine (T:A-T) and protonated cytosine recognizing guanine (C$^+$:G-C). See Best et al., *J. Am. Chem. Soc.*, 1995, 117, 1187–1193). In a less well-studied triplex motif, purine-rich oligonucleotides bind to purine targets of double-stranded DNA. The orientation of the third strand in this motif is anti-parallel to the purine Watson-Crick strand, and the specificity is derived from guanine recognizing guanine (G:G-C) and thymine or adenine recognizing adenine (A:A-T or T:A-T). See Greenberg et al., *J. Am. Chem. Soc.*, 1995, 117, 5016–5022.

Homopyrimidine PNAs form highly stable PNA:DNA-PNA complexes with complementary oligonucleotides. The formation of triple helix structures involving two PNA strands and one nucleotide strand has been previously reported in U.S. Pat. No. 6,228,982 entitled Double-Stranded Peptide Nucleic Acids, the contents of which are incorporated herein by reference in their entirety. The formation of triplexes in which the Hoogsteen strand is parallel to the DNA purine target strand is preferred to formation of anti-parallel complexes. This allows for the use of bis-PNAs to obtain triple helix structures with increased pH-independent thermal stability using pseudoisocytosine instead of cytosine in the Hoogsteen strand. See, Egholm et al., *J. Am. Chem. Soc.*, 1992, 114, 1895–1897, also see Published PCT application WO 96/02558 the entire contents of each of which are incorporated herein by reference.

Peptide nucleic acids have been shown to have higher binding affinities (as determined by their melting temperatures) for both DNA and RNA than that of DNA or RNA to either DNA or RNA. This increase in binding affinity makes these peptide nucleic acid oligomers especially useful as molecular probes and diagnostic agents for nucleic acid species.

It has been previously shown that a carbazole-like 2'-deoxycytidine analog incorporated into oligonucleotides will pair specifically with guanine in complementary RNA in a duplex motif (U.S. Pat. No. 5,502,177, issued Mar. 26, 1996, entitled Pyrimidine Derivatives for Labeled Binding Partners; Matteucci, M. D., von Krosigk, U., *Tetrahetron Letters*, 1996, 37, 5057–5060; Kuei-Ying, L., et al., *J. Am. Chem.*, 1995, 117, 3873–3874).

The current limitations in the formation of triplex structures (such as the limitation to homopurine targets) is one of the major difficulties for sequence-specific recognition of defined sites of DNA by peptide nucleic acids. See Nielsen, *J. Am. Chem. Soc.*, 1996, 118, 2287–2288. Accordingly, there is a need for new PNA oligomers containing nucleobase-binding moieties that can bind Watson-Crick base pairs, preferentially within the pyrimidine triple helix motif.

SUMMARY OF THE INVENTION

Provided in accordance with the present invention are oligomeric compounds, particularly peptide nucleic acids, comprising a moiety having the Formula I:

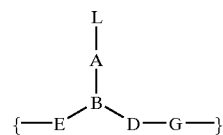

wherein:
L is an adenosine-thymidine nucleobase pair recognition moiety;
A is a single bond, a methylene group or a group of formula:

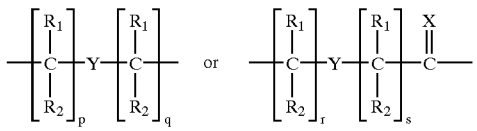

where:
X is O, S, Se, NR$_3$, CH$_2$ or C(CH$_3$)$_2$;
Y is a single bond, O, S or NR$_4$;
each p, q, r and s is, independently, zero or an integer from 1 to 5;
each R$_1$ and R$_2$ is, independently, selected from the group consisting of hydrogen, (C$_1$–C$_4$)alkyl which may be hydroxy- or alkoxy- or alkylthio-substituted, hydroxy, alkoxy, alkylthio, amino and halogen; and
each R$_3$ and R$_4$ is, independently, selected from the group consisting of hydrogen, (C$_1$–C$_4$)alkyl, hydroxy- or alkoxy- or alkylthio-substituted (C$_1$–C$_4$) alkyl, hydroxy, alkoxy, alkylthio and amino;
B is N or R$_3$—N$^+$, where R$_3$ is as defined above;
E is CR$_6$R$_7$, CHR$_6$CHR$_7$ or CR$_6$R$_7$CH$_2$, where R$_6$ is hydrogen and R$_7$ is selected from the group consisting of the side chains of naturally occurring alpha amino acids, or R$_6$ and R$_7$ are independently selected from the group consisting of hydrogen, (C$_2$–C$_6$)alkyl, aryl, aralkyl, heteroaryl, hydroxy, (C$_1$–C$_6$)alkoxy, (C$_1$–C$_6$) alkylthio, NR$_3$R$_4$ and SR$_5$, where R$_3$ and R$_4$ are as defined above, and R$_5$ is hydrogen, (C$_1$–C$_6$)alkyl, hydroxy-, alkoxy-, or alkylthio- substituted (C$_1$–C$_6$) alkyl, or R$_6$ and R$_7$ taken together complete an alicyclic or heterocyclic system;
D is CR$_6$R$_7$, CH$_2$CR$_6$R$_7$ or CHR$_6$CHR$_7$, where R$_6$ and R$_7$ are as defined above; and
G is —NR$_3$CO—, —NR$_3$CS—, —NR$_3$SO— or —NR$_3$SO$_2$—, in either orientation, where R$_3$ is as defined above.

In preferred embodiments, the monomeric unit has the Formula II:

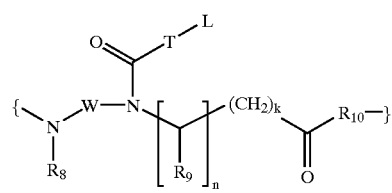

wherein:
R$_8$ is H, COCH$_3$ or an amino protecting group;
R$_9$ is hydrogen or a side chain of a naturally occurring amino acid;

$R_{10}$ is O, NH, O-alkylene or a lysine residue;

W is —$(CH_2)_m$— where m is from 0 to about 6, or

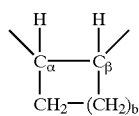

where b is an integer from 0 to 4;

k is from 0 to about 5;

n is 0 or 1;

L has the formula

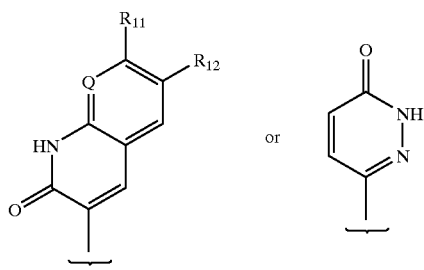

Q is CH or N;

$R_{11}$ and $R_{12}$ are each H;

or $R_{11}$ and $R_{12}$ together with the carbon atoms to which they are attached form a phenyl group;

T has the formula:

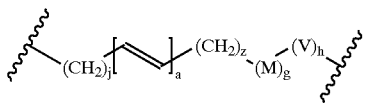

j and z are each, independently, from 0 to about 5 with the sum of j and z being from 1 to 7;

M is C (=O), S(O)$_2$, phenyl or P(O)$_2$;

V is NH, S, or CH$_2$; and a, h and g are each independently 0 or 1.

Also provided in accordance with the present invention are monomeric compounds having the Formula III:

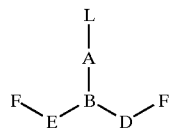

wherein:

L, A, B, D and E have the meaning described above, and each F is, independently, NHR$_3$ or NPgR$_3$, where R$_3$ is as defined above, and Pg is an amino protecting group.

In preferred embodiments, the monomeric compounds of the invention have the Formula IV:

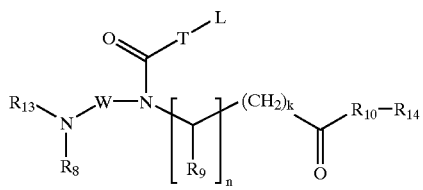

wherein:

$R_8$, $R_9$, T, L, W, k and n have the meaning described above, and $R_{13}$ and $R_{14}$ are each independently H or a protecting group.

In some preferred embodiments of the compounds of the invention, g and h are each 0. In more preferred embodiments g and h are each 0, and a is 0. In further preferred embodiments a is 0, g is 0, X is NH and h is 1.

In preferred embodiments L is 3-oxo-2,3-dihydropyridazin-1-yl, which has the formula:

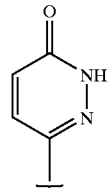

In especially preferred embodiments L is 3-oxo-2,3-dihydropyridazin-1-yl and T is —CH$_2$—CH$_2$—NH—.

In some preferred embodiments $R_4$ and $R_5$ are each H. In further preferred embodiments $R_4$ and $R_5$ together with the atoms to which they are attached form a phenyl ring.

In some preferred embodiments Q is N; and in other preferred embodiments Q is CH.

Preferably, T is lower alkyl or alkylamino. In especially preferred embodiments T is —CH$_2$— or —CH$_2$—CH$_2$—NH—.

In some preferred embodiments W is —$(CH_2)_m$—, preferably —$(CH_2)_2$—. In other preferred embodiments W has the formula:

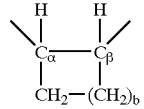

where b is preferably an integer between 0 and 4, with 2 and 3 being particularly preferred. In further preferred embodiments at least one of Cα or Cβ is in the S configuration.

In some preferred embodiments, the compounds of the invention are peptide nucleic acids. In other preferred embodiments the compounds of the invention comprise a plurality of peptide nucleic acid oligomers, preferably 2 oligomers, that are linked by linking groups, wherein at least one of the peptide nucleic acid oligomers comprises a moiety having Formula II. In particularly preferred embodiments two peptide nucleic acid oligomers are linked by a linking moiety, which is preferably 8-amino-3,6-dioxaoctanoic acid.

Some particularly preferred embodiments of the compounds of the invention have the formula:

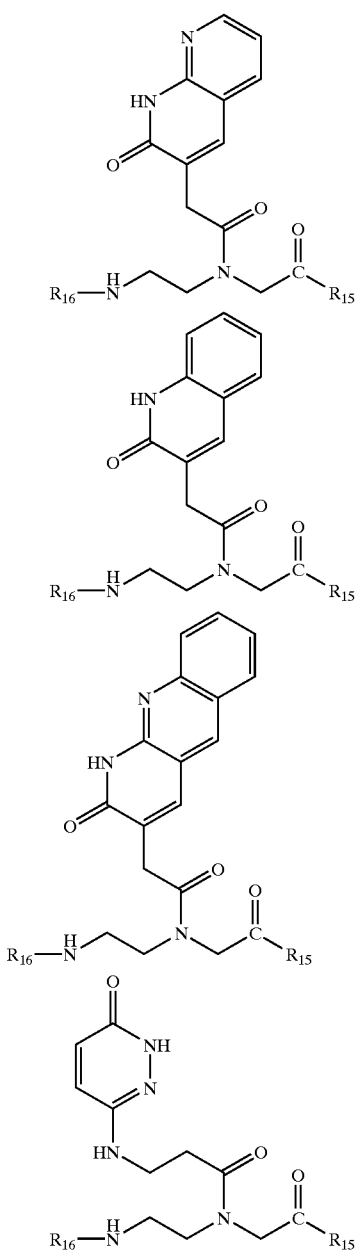

wherein $R_{15}$ is OH or a protecting group; and $R_{16}$ is H or a protecting group.

Also provided in accordance with the present invention are compositions, preferably triplex compounds, comprising a single stranded DNA coding for a sequence suspected of being implicated in a disease state and containing one or more thymine residues; a first peptide nucleic acid oligomer that comprises a region that is complementary to a region of the single stranded nucleic acid; and a second peptide nucleic acid oligomer comprising a sequence that is complementary to a region of the single stranded nucleic acid, the second peptide nucleic acid oligomer having at one or more positions complementary to the thymine residues of the single stranded nucleic acid a residue having a nonpurine nucleobase, preferably a residue of Formula II.

The present invention also provides methods for forming a triplex compound comprising the steps of:

(a) selecting a single stranded nucleic acid containing one or more thymine residues;

(b) providing a first oligomer that comprises a region that is complementary to a region of the single stranded nucleic acid;

(c) contacting the single stranded nucleic acid and the first oligomer with a second oligomer, where the second oligomer is a peptide nucleic acid oligomer comprising a sequence that is complementary to a region of the single stranded nucleic acid and has at one or more positions complementary to the thymine residues of the single stranded nucleic acid a residue of Formula II, for a time and under conditions effective to form the triple helix compound. Preferably, the first oligomer is PNA or DNA.

In some preferred embodiments of the methods of the invention the first oligomer is oriented antiparallel to the single stranded nucleic acid, and the second oligomer is oriented parallel to the single stranded nucleic acid in the triplex compound. In particularly preferred embodiments the triplex compound has the formula PNA-DNA-PNA.

Preferably, the single stranded nucleic acid is DNA or RNA.

In further preferred embodiments the first oligomer is a peptide nucleic acid, and the first oligomer is linked to the second oligomer by a linking moiety.

In some preferred embodiments of the methods of the invention the first and second oligomers are each from 4 to about 20 nucleobases in length.

The present invention also provides methods for the detection of a chemical or microbiological entity which contains a known nucleobase sequence comprising:

selecting a nucleobase sequence from the chemical or microbiological entity which contains one or more thymine residues;

providing a PNA oligomer that contains a region that complementary to the selected nucleobase sequence;

contacting the selected nucleobase sequence of the chemical or microbiological entity and the complementary PNA oligomer with a further peptide nucleic acid oligomer which contains a sequence that is complementary to the selected nucleobase sequence, where the further peptide nucleic acid oligomer has at one or more positions complementary to the thymine residues of the selected nucleobase sequence a residue of Formula II, to form a triple helix compound; and detecting the triple helix compound.

Methods are also provided for the sequence-specific recognition of a double-stranded polynucleotide, comprising contacting the polynucleotide with a compound having a residue of Formula II.

Methods are also provided for the sequence-specific recognition of a double-stranded polynucleotide, comprising contacting the polynucleotide with an oligomeric compound that binds to the polynucleotide to form a triplex structure, wherein the oligomeric compound comprises a monomeric unit having Formula I, more preferably Formula II.

DESCRIPTION OF PREFERRED EMBODIMENTS

In one aspect, the present invention provides novel oligomeric compounds, especially peptide nucleic acids, that are useful as research reagents, and as specific probes for complementary nucleic acid. The present invention also provides monomeric synthons useful in the preparation of the oligomeric compounds.

In preferred embodiments the compounds of the invention contain a moiety of Formula I:

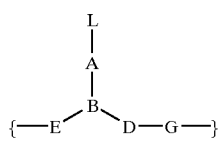

I wherein:
L is an adenosine-thymidine nucleobase pair recognition moiety;
A is a single bond, a methylene group or a group of formula:

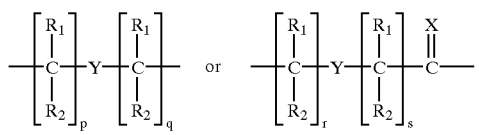

where:
X is O, S, Se, $NR_3$, $CH_2$ or $C(CH_3)_2$;
Y is a single bond, O, S or $NR_4$;
each p, q, r and s is, independently, zero or an integer from 1 to 5;
each $R_1$ and $R_2$ is, independently, selected from the group consisting of hydrogen, $(C_1–C_4)$alkyl which may be hydroxy- or alkoxy- or alkylthio-substituted, hydroxy, alkoxy, alkylthio, amino and halogen; and
each $R_3$ and $R_4$ is, independently, selected from the group consisting of hydrogen, $(C_1–C_4)$alkyl, hydroxy- or alkoxy- or alkylthio-substituted $(C_1–C_4)$ alkyl, hydroxy, alkoxy, alkylthio and amino;
B is N or $R_3$—$N^+$, where $R_3$ is as defined above;
E is $CR_6R_7$, $CHR_6CHR_7$ or $CR_6R_7CH_2$, where $R_6$ is hydrogen and $R_7$ is selected from the group consisting of the side chains of naturally occurring alpha amino acids, or $R_6$ and $R_7$ are independently selected from the group consisting of hydrogen, $(C_2–C_6)$alkyl, aryl, aralkyl, heteroaryl, hydroxy, $(C_1–C_6)$alkoxy, $(C_1–C_6)$ alkylthio, $NR_3R_4$ and $SR_5$, where $R_3$ and $R_4$ are as defined above, and $R_5$ is hydrogen, $(C_1–C_6)$alkyl, hydroxy-, alkoxy-, or alkylthio-substituted $(C_1–C_6)$ alkyl, or $R_6$ and $R_7$ taken together complete an alicyclic or heterocyclic system;
D is $CR_6R_7$, $CH_2CR_6R_7$ or $CHR_6CHR_7$, where $R_6$ and $R_7$ are as defined above; and
G is —$NR_3CO$—, —$NR_3CS$—, —$NR_3SO$— or —$NR_3SO_2$—, in either orientation, where $R_3$ is as defined above.

In more preferred embodiments the compounds of the present invention contain a moiety of Formula II:

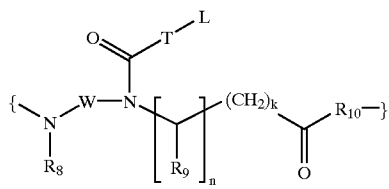

II wherein:
$R_8$ is H, $COCH_3$ or an amino protecting group;
$R_9$ is hydrogen or a side chain of a naturally occurring amino acid;
$R_{10}$ is O, NH, O-alkylene or a lysine residue;
W is —$(CH_2)_m$— where m is from 0 to about 6, or

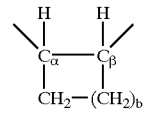

where b is an integer from 0 to 4;
k is from 0 to about 5;
n is 0 or 1;
L has the formula

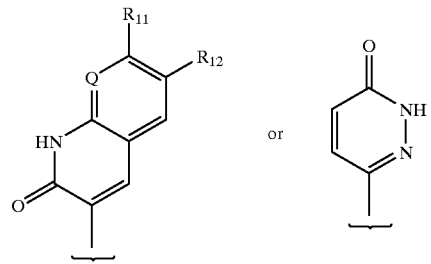

Q is CH or N;
$R_{11}$ and $R_{12}$ are each H;
or $R_{11}$ and $R_{12}$ together with the carbon atoms to which they are attached form a phenyl group;
T has the formula:

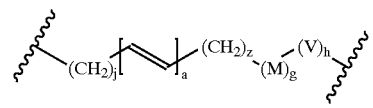

j and z are each, independently, from 0 to about 5 with the sum of j and z being from 1 to 7;
M is C(=O), $S(O)_2$, phenyl or $P(O)_2$;
V is NH, S, or $CH_2$; and
a, h and g are each independently 0 or 1.

Preferred embodiments of the compounds of the invention include oligomeric compounds that contain one or more moieties of Formula II. There can be as few as one moiety of Formula II in the oligomer, or the majority of monomeric units in the oligomer can be moieties of Formula II.

Further preferred embodiments of the compounds of the invention include two PNA oligomers that are linked together by one or more linking moieties, wherein one or both of the PNA oligomers contain at least one moiety of Formula II ("bis-PNA oligomers"). The present invention also includes higher order linked PNA oligomers, wherein a plurality of PNA oligomers are linked by linking moieties, wherein one or more of the linked PNA oligomers contain at least one moiety of Formula II.

As used herein, the term "peptide nucleic acid" (PNA) refers to compounds that in some respects are analogous to oligonucleotides, but which differ in structure. In peptide nucleic acids, the deoxyribose backbone of oligonucleotides has been replaced with a backbone having peptide linkages. Each subunit has attached a naturally occurring or non-naturally occurring base. One such backbone is constructed of repeating units of N-(2-aminoethyl)glycine linked through amide bonds.

The present invention also provides PNA monomers, which are useful, for example, in the preparation of the PNA oligomers of the invention. In some preferred embodiments the PNA monomers of the present invention have an achiral backbone. One preferred example of an achiral PNA backbone is the 2-aminoethylglycine backbone. See, for example, International patent applications WO 92/20702 and WO 92/20703, the contents of each of which are incorporated herein by reference.

In other preferred embodiments, the invention provides PNA monomers containing a chiral backbone. In some preferred embodiments, chirality is introduced into the PNA backbone through the incorporation of an aliphatic cyclic structure. In one particularly preferred embodiment, the aliphatic cyclic structure includes the a and f carbons of the 2-aminoethyl portion of an aminoethylglycine backbone, and has the formula:

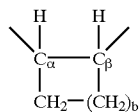

where b is an integer from 0 to 4; α denotes the carbon that is adjacent to the glycyl amino group; and β denotes the carbon that is one adjacent to the α carbon. The aliphatic cyclic structure may be a 4, 5, 6 or 7 membered ring. In preferred embodiments the aliphatic cyclic structure is a 5 or 6 membered ring, with 6 being especially preferred.

The use of optically active reagents permits the synthesis of pure SS, RR, SR, and RS isomers. The SS isomer is preferred in some embodiments of the present invention.

Typically, monomers having a chiral backbone are prepared using (1,2)-diaminocyclohexane, which is available as the cis, or the trans isomer. The cis-(1,2)-diaminocyclohexane is a meso compound. Use of such meso compound requires resolution of a racemic mixture. The trans-(1,2)-diaminocyclohexane is commercially available in enantiomerically pure form, making it well suited for monomers of predetermined chirality about both the Cα and the Cβ of the 2-aminoethyl portion of the backbone.

The diamine is typically protected at one of the amino groups with di-t-butylpyrocarbonate (Boc$_2$O), followed by N-alkylation with methyl bromoacetate to give the chiral backbone. Coupling of a ligand (suitably protected where necessary) with the chiral backbone using DCC/DhbtOH followed by basic hydrolysis will give the desired monomer containing the chiral backbone. In this manner the SS and RR monomers may be synthesized. The RS and the SR isomers can be synthesized using the cis-(1,2)-diaminocyclohexane, and resolving the resulting racemic mixture. Resolution can be achieved, for example, by liquid chromatography.

The resulting monomer has increased conformational restriction, and is expected to increase the lipophilicity of the monomer. PNA monomers containing chiral backbones are disclosed in copending U.S. Pat. No. 5,977,296, the contents of which are hereby incorporated by reference in their entirety.

PNA oligomers comprising at least one chiral monomer of the invention are prepared in accordance with methods known to those skilled in the art. Established methods for the stepwise or fragmentwise solid-phase assembly of amino acids into peptides normally employ a beaded matrix of slightly cross-linked styrene-divinylbenzene copolymer, the cross-linked copolymer having been formed by the pearl polymerization of styrene monomer to which has been added a mixture of divinylbenzenes. A level of 1–2% cross-linking is usually employed. Such a matrix also can be used in solid-phase PNA synthesis in accordance with the present invention.

In some preferred embodiments, the PNA oligomers of the invention contain one or more chiral monomeric subunits. The PNA oligomers of the invention can contain one chiral subunit, a plurality of chiral subunits, or can be composed primarily or entirely of chiral subunits.

Preferably, the PNA oligomer is prepared to be complementary to a target molecule, i.e. at least a portion of the PNA oligomer has the ability to hybridize due to Watson-Crick base pair attraction to the target molecule, or due to Hoogsteen hydrogen bonds in triplex structures.

In preferred embodiments the aminoalkyl nitrogen of the PNA backbone can bear a substituent, which is denoted $R_8$ in Formulas II and IV. Preferably, $R_8$ is hydrogen, COCH$_3$, or an amino protecting group.

Functional groups present on the compounds of the invention may contain protecting groups. Protecting groups are known per se as chemical functional groups that can be selectively appended to and removed from functionalities, such as amino groups and carboxyl groups. These groups are present in a chemical compound to render such functionality inert to chemical reaction conditions to which the compound is exposed. Any of a variety of protecting groups may be employed with the present invention. One preferred protecting group for amino groups is the Boc group. Other preferred protecting groups according to the invention may be found in Greene, T. W. and Wuts, P. G. M., "*Protective Groups in Organic Synthesis*" 2d. Ed., Wiley & Sons, 1991.

Substituent $R_9$ is hydrogen, or the sidechain of a naturally occurring amino acid. As used herein, the term "amino acid" denotes a molecule containing both an amino group and a carboxyl group, and has the general formula CH(COOH)(NH$_2$)-(side chain). A naturally occurring amino acid is an amino acid that is found in nature; i.e., one that is produced by living organisms. One representative amino acid side chain is the lysyl side chain, —(CH$_2$)$_4$—NH$_2$. Other representative naturally occurring amino acids can be found, for example, in Lehninger, *Biochemistry*, Second Edition, Worth Publishers, Inc, 1975, pages 73–77.

In preferred embodiments $R_{10}$ is O, NH, O-alkylene, or a lysine residue. As used herein, the term "alkyl" includes straight-chain, branched and cyclic hydrocarbon groups such as, for example, ethyl, isopropyl and cyclopropyl groups. Preferred alkyl groups have 1 to about 10 carbon atoms. The term "alkylene" denotes divalent alkyl groups; i.e., methylene (—CH$_2$—), ethylene (—CH$_2$CH$_2$—), propylene (—CH$_2$CH$_2$CH$_2$—), etc.

The term "alkoxy" has its accustomed meaning as an —O-alkyl group. An "alkylthio" group denotes a group of formula —S-alkyl. Halogens include fluorine, chlorine, Bromine, and iodine.

The term aryl is intended to denote monocyclic and polycyclic aromatic groups including, for example, phenyl, naphthyl, xylyl, pyrrole, and furyl groups. Although aryl groups (e.g., imidazole groups) can include as few as 3 carbon atoms, preferred aryl groups have 6 to about 14 carbon atoms, more preferably 6 to about 10 carbon atoms. Aralkyl and alkaryl groups according to the invention each include alkyl and aryl portions. Aralkyl groups are attached through their alkyl portions, and alkaryl groups are attached through their aryl portions. Benzyl groups provide one example of an aralkyl group, and p-toluyl provides an example of an alkaryl group. As used herein, the term "heterocyclic" denotes a ring system that includes at least one hetero atom, such as nitrogen, sulfur or oxygen. The term "heteroaryl" specifically denotes aryl heterocyclic groups.

In the context of this invention, the term "polynucleotide" refers to an oligomer or polymer of ribonucleic acid or deoxyribonucleic acid.

In the PNA monomers of the present invention, an adenosine-thymidine nucleobase pair recognition moiety is connected to the PNA backbone by a tether, denoted as substituent A in Formula I. In some preferred embodiments, the tether terminates in a carbonyl group, which is preferably attached to a nitrogen atom of the PNA backbone. In more preferred embodiments the tether terminates in a carbonyl group which is attached to the glycyl nitrogen of a 2-aminoethylgylcine backbone. In further preferred embodiments the tether terminates in a carbonyl group which is attached to the glycyl nitrogen of a chiral derivative of a 2-aminoethylgylcine backbone, wherein the a and f carbons of the 2-aminoethyl portion of the aminoethylglycine backbone participate in an alicyclic ring, as described above.

In some preferred embodiments the portion of the tether attached to the PNA-bound carbonyl group has the formula:

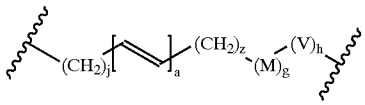

where j and z are each, independently, from 0 to about 5 with the sum of j and z being from 1 to 7; G is C(=O), S(O)$_2$, phenyl or P(O)$_2$; X is NH, S, or CH$_2$; and a, h and g are each independently 0 or 1. In some preferred embodiments, the tether is alkyl or alkylamino, preferably having fewer than about six carbons, with two carbons being especially preferred. Particularly preferred tethers include methylene groups (—CH$_2$) and ethylamino groups (—CH$_2$—CH$_2$—NH—). It is desirable to select the tether such that the ligand has the proper-placement and orientation to maximize the interaction between the ligand and the AT pair (especially thymine) residing on complementary positions in the triplex structures. Preferably, the tether is linear and contains from 3 to 6 atoms in the linear chain, more preferably 4 or 5 atoms, with 4 being especially preferred.

In some preferred embodiments, at least one PNA monomer having a chiral center in the ethyl portion thereof is incorporated into the PNA oligomer at the site where'a mismatch (i.e. variability of the target molecule) is expected or known to occur.

The PNA oligomers of the invention can have a variety of substituents attached thereto. For example, in some preferred embodiments the oligomers of the invention have a conjugate group attached, to afford easier detection or transport of the PNA. The conjugate group can be a reporter enzyme, a reporter molecule, a steroid, a carbohydrate, a terpene, a peptide, a protein, an aromatic lipophilic molecule, a non aromatic lipophilic molecule, a phospholipid, an intercalator, a cell receptor binding molecule, a crosslinking agent, a water soluble vitamin, a lipid soluble vitamin, an RNA cleaving complex, a metal chelator, a porphyrin, an alkylator, and polymeric compounds such as polymeric amines, polymeric glycols and polyethers. PNAs of the present invention can include one or more conjugates attached directly or through an optional linking moiety. When so derivatized, the PNA is useful, for example, as a diagnostic or therapeutic agent, to render other properties to a complementary nucleic acid or triplex in a test structure or to transfer a therapeutic or diagnostic agent across cellular membranes.

The conjugate group can be attached to the PNA oligomers of the invention anywhere on the PNA backbone, either on the monomeric unit of Formula II, or elsewhere on the PNA. The conjugate group can be attached to a monomer, and incorporated into the PNA oligomer. Alternatively, the conjugate group can be attached to the PNA oligomer after assembly from constituent monomers. Methods for the attachment of conjugate groups can be found in U.S. application Ser. No. 08/319,411 filed Oct. 6, 1994, the contents of which are incorporated by reference in their entirety.

In some particularly preferred embodiments, the oligomeric compounds of the invention bear a reporter molecule such as a chromaphore or a fluorophore, for example fluorescein or rhodamine. For example, PNA oligomers of the invention, including those having at least one chiral monomer, are easily derivatized to include a fluorescein or rhodamine using an aminohexanoic linker group. These derivatized PNA oligomers are well suited for use as probes for a section of DNA of interest. Those skilled in the art will appreciate that.the present invention is amenable to a variety of other types of labeling reagents and linkers.

The adenosine-thymidine nucleobase pair recognition moieties of the compounds of the present invention, represented by substituent L in Formulas I–IV, are surrogates for nucleobases that are ordinarily found in triple helix strands at positions complementary to thymidine (i.e., complementary to adenosine-thymidine base pairs).

Triplex structures which incorporate oligomers of the invention, which have a monomeric unit containing an adenosine-thymidine nucleobase pair recognition moiety at a position complementary to a Watson-Crick adenosine-thymidine base pair (that is, which have a monomeric unit of Formula I or II at a position complementary to the Watson-Crick adenosine-thymidine base pair), display increased binding (i.e., have a higher melting temperature) relative to otherwise identical triplex structures having a natural nucleobase at the site complementary to the Watson-Crick adenosine-thymidine base pair. Accordingly, the compounds of the invention are able to "recognize" thymine residues in triple helix structures by this increased binding. Thus, the term "adenosine-thymidine nucleobase pair recognition moiety" as defined herein is a non-natural heterocyclic moiety that, when substituted for a natural nucleobase able to bind to Watson-Crick base pairs in triple helix structures, forms a triplex structure having increased binding relative to identical triplexes not having the adenosine-thymidine nucleobase pair recognition moiety.

In some preferred embodiments of the invention the adenosine-thymidine nucleobase pair recognition moiety is a C-pyrimidine (e.g. a pyrimidine in which the linkage connecting the pyrimidine to the backbone either with or without a tether is made through a carbon and not a nitrogen atom) or an iso-pyrimidine.

The adenosine-thymidine nucleobase pair recognition moieties and tethers of the compounds of the invention, represented by —T—L in Formulas I–IV, are selected to afford the maximum affinity for complementary thymine residues in the DNA portion of triplex structures, for example PNA:DNA-PNA triplex structures. Although not wishing to be bound by a specific theory, it is believed that in order to recognize thymine of a T-A base-pair in the major groove of a Watson and Crick double helix structure, it is preferred that the ligand be connected to the PNA backbone with a tether that allows sufficient freedom to circumvent the 5-methyl group of thymine. In addition, the selected ligand preferably has a hydrogen donor that can bind to the 4-oxo group of thymine. A further useful feature is the presence of a second functionality, located on or attached to the ligand, that can act as a hydrogen acceptor to form a hydrogen bond to the N-6 hydrogen atoms of adenine. It is believed that the compounds of the present invention that recognize thymine in a Watson and Crick double helix structure possess these attributes.

Adenosine-thymidine nucleobase pair recognition moieties can be selected by methods known to those of skill in the art. For example, adenosine-thymidine nucleobase pair recognition moieties can be selected by appropriate computer modeling programs, such as the Insight II and Discover programs, available from Biosym, San Diego, Calif.

In some preferred embodiments adenosine-thymidine nucleobase pair recognition moieties have the formula:

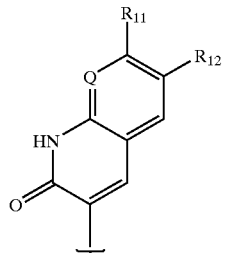

where Q is CH or N; $R_{11}$ and $R_{12}$ are each H; or $R_4$ and $R_5$ together with the carbon atoms to which they are attached form a phenyl group. In particularly preferred embodiments the adenosine-thymidine nucleobase pair recognition moieties are attached to aminoethylglycine PNA backbones through methylene tethers.

In more preferred embodiments, the tether and adenosine-thymidine nucleobase pair recognition moiety together have one of the formulas:

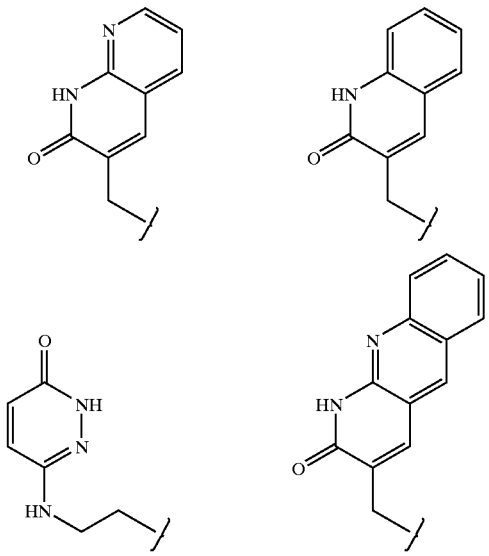

One particularly preferred adenosine-thymidine nucleobase pair recognition moiety is the 3-oxo-2,3-dihydropyridazin-1-yl group. In particularly preferred embodiments 3-oxo-2,3-dihydropyridazin-1-yl adenosine-thymidine nucleobase pair recognition moieties are attached to aminoethylglycine PNA backbones through ethylamino tethers.

In particularly preferred embodiments, monomers of the present invention have one of the formulas:

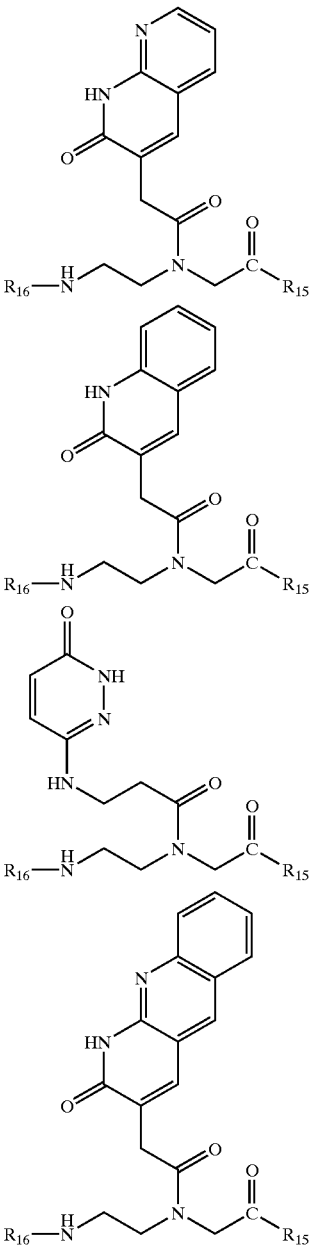

wherein $R_{15}$ is OH or a protecting group; and $R_{16}$ is H or a protecting group.

The PNA oligomers and linked PNA oligomers of the present invention are useful for forming $PNA_2$/DNA triple helix structures. Preferred embodiments of the compounds of the invention include triple helix (i.e., triplex) PNA.DNA-PNA structures in which at least one of the PNA strands contains at least one monomer moiety in accordance with Formula I, preferably Formula II. In more preferred embodiments the two PNA oligomers in the PNA.DNA-PNA are constituent members of a bis-PNA; i.e., the two PNA oligomers are linked together by one or more linking moieties ("linking groups").

Linking moieties that link PNA oligomers in compounds of the invention are selected such that the PNA oligomers have sufficient freedom to permit formation of the triplex structure. A variety of groups can be used as linking moieties, for example "egl groups" (ethylene glycol) and "Aha groups" (amino hexanoic acid) linked together by amino acid groups. A further linking segment includes the above Aha groups interspaced with a-amino acids particularly glycine or lysine. One especially preferred linking moiety is one or more 8-amino-3,6-dioxaoctanoic acid residues.

A wide range of other compounds are also useful for the linking segment and thus are included within the scope of the present invention. Generally the linking segment is a compound having a primary amino group and a carboxy group separated with a space spanning group, wherein the space spanning group consists of one or more functional groups. Some representative space spanning groups are $C_1$ to $C_{20}$ alkyl, $C_2$ to $C_{20}$ alkenyl, $C_2$ to $C_{20}$ alkynyl, $C_1$ to $C_{20}$ alkanoyl having at least one O or S atom, $C_7$ to $C_{34}$ aralkyl, $C_6$–$C_{14}$ aryl and amino acids. Preferred alkanoyl groups can have from 1 to 10 hetero atoms such as O or S. Preferred alkanoyl groups include methyl, ethyl and propyl alkanoxy particularly polyethoxy, i.e., ethylene glycol. Amino acids including D, L, and DL isomers of α-amino acids as well as longer chain amino acids may also be linked together to form a linking segment. A particularly preferred amino acid is hexanoic amino acid. Aralkyl groups used as space spanning groups may have the amino or the carboxy group located on the aromatic ring or spaced with one or more $CH_2$ groups wherein the total number of $CH_2$ groups is less than or equal to twenty. The position of substitution in an aralkyl linked PNA may be varied; however, ortho and meta are presently preferred because substitution at these positions, especially ortho, induce the bis PNA to be bent, thus facilitating location of the two joined peptide nucleic acid strands in spacial locations parallel to one another. Another group of bis PNAs that include induced bends are those that incorporate cis-alkenyl linkers or a proline linker.

In selecting a linking segment, one consideration is compatibility with PNA chemistry, and the ability to link a functional group on one end of a PNA to a functional group on one end of a second PNA. Also, the linking segment can be selected so as to be flexible, such that the two linked PNAs are able to interact with ssDNA, ssRNA or dsDNA in similar fashion to the way that two independent PNA single strands would so interact. Some preferred linking segments that have been shown to be effective have lengths of 23 and 24 atoms.

The term "complementary" as used herein has its accustomed meaning as the ability to form either Watson-Crick or Hoogsteen bonds within a nucleic acid (RNA or DNA) duplex, a PNA-nucleic acid duplex, a triplex structure including nucleic acid, PNA, or mixtures thereof.

In the $PNA_2$/DNA compounds of the invention, PNA oligomers are typically prepared as Watson-Crick antiparallel strands, and additional PNA oligomers are prepared as parallel (e.g. Hoogsteen) strands. In one preferred embodiment, the PNA monomers of the invention are used in the Hoogsteen strand in positions that are complementary to thymine or uracil in the target nucleic acid to increase the binding of the Hoogsteen strand, and hence increase the melting temperature (Tm) of the resulting triple helix that is formed.

As used herein, the term "binding affinity" refers to the ability of a duplex to bind to a target molecule via hydrogen bonds, van der Waals interactions, hydrophobic interactions, or otherwise. Target molecules include single stranded DNA or RNA, as well as duplexes between DNA, RNA, and their analogs such as PNA.

As used herein, the term "nucleobase" has its accustomed meaning as a heterocyclic base that is capable of participating in Watson-Crick or Hoogsteen bonds in nucleic acid duplex or triplex structures. These include the natural nucleobases adenine, guanine, cytosine, thymine and uracil, as well as unnatural nucleobases (i.e., nucleobase analogs) that are known to mimic the function of the natural nucleobases in DNA or RNA analogs. Representative nucleobase analogs can be found in, for example, *Antisense Research and Application*, Ed. S. T. Crooke and B. Lebleu, Chapter 15, CRC Press, 1993, and U.S. Pat. No. 3,687,808 to Merigan, et al., the contents of which are hereby incorporated by reference in their entirety.

PNA oligomers of the present invention form triple helix structures with nucleic acid targets wherein the PNA oligomer has an increased binding affinity relative to previously reported PNA oligomers. The PNA oligomers and linked PNA oligomers having PNA monomer moieties of Formula I–IV in positions complementary to thymine or uracil in a nucleic acid target show increased binding specificity relative to the same triplex structure formed with linked PNA oligomers having adenine in positions that are complementary to thymine or uracil(see Example 5).

Thus, the PNA oligomers and linked PNA oligomers of the invention find use in applications where it is desired to detect or identify oligonucleotide sequences containing thymidine residues. Accordingly, the PNA oligomers of the present invention are useful as research reagents and as diagnostic tools. In one preferred embodiment, the oligomers and linked oligomers of the invention are useful for the detection of nucleic acid sequences suspected of being implicated in a disease state, which contain one or more thymine residues. Accordingly, the present invention includes triplex structures containing nucleic acid sequences suspected of being implicated in a disease state, and at least one PNA oligomer of the invention.

In some preferred embodiments, compositions of the invention including single stranded DNA coding for a sequence suspected of being implicated in a disease state and containing one or more thymine residues; a first peptide nucleic acid that comprises a region that is complementary to a region of the single stranded nucleic acid; and a second peptide nucleic acid comprising a sequence that is complementary to a region of the single stranded nucleic acid, the peptide nucleic acid oligomer having at one or more positions complementary to the thymine residues of the single stranded nucleic acid a residue of Formula I, preferably Formula II.

The present invention also provides methods for forming a triple helix compound comprising (a) selecting a single stranded nucleic acid containing one or more thymine residues; (b) providing a first oligomer that comprises a region that is complementary to a region of the single stranded nucleic acid; (c) contacting the single stranded nucleic acid and the first oligomer with a second oligomer, wherein the second oligomer comprises a sequence that is complementary to a region of the single stranded nucleic acid, and has at one or more positions complementary to the thymine residues of the single stranded nucleic acid a residue of Formula I or II for a time and under conditions effective to form the triple helix compound.

In some preferred embodiments, the single stranded nucleic acid will be selected for its biological activity, such as its pathogenic properties. The first oligomer will be then be synthesized to include a region that is complementary to a region of the single stranded nucleic acid, preferably a region with more than one thymine residue. The contacting of the single stranded nucleic acid and the first oligomer with the second oligomer may be accomplished by a variety of means, known in the art, that promotes triplex formation. See for example, U.S. patent application, Ser. No. 08/088, 661, for in vitro determination of a nucleic acid in a sample which may be made by pipetting one or more solutions containing said first and second oligomer as well as optionally all reagents necessary for effective triplex formation to the sample.

In preferred embodiments, methods are provided for the detection of a chemical or microbiological entity which contains a known nucleobase sequence comprising a) selecting a nucleobase sequence from the chemical or microbiological entity which contains one or more thymine residues; b) providing a PNA oligomer that contains a region that is complementary to the selected nucleobase sequence; c) contacting the selected nucleobase sequence of the chemical or microbiological entity and the complementary PNA oligomer with a further PNA oligomer which contains a sequence that is complementary to the selected nucleobase sequence, wherein the further PNA oligomer has at one or more positions complementary to the thymine residues of the selected nucleobase sequence a residue of Formula I or II to form a triple helix compound; and d) detecting the triple helix compound.

Detection of the triple helix compound can be accomplished by detection of a reporter molecule, such as a chromophore or fluorophore, that is bound covalently or non-covalently to the compound of the invention as described above. Useful conjugates are described in WO 95/14708, WO 95/16202 and WO 92/20703. Alternatively, detection may be by any of several means, including Tm studies, mass measurements and crosslinking studies.

The further PNA oligomer can alternatively have attached a moiety enabling immobilization on a solid support, such as polystyrene. One example of such a moiety is biotin which can be bound to polystyrene via a coating of streptavidine. Formation of the triple helical structure can then be accomplished by labels attached to either the other PNA oligomer or to the nucleobase sequence a chemical entity.

Chemical entities are understood to include chemically synthesized oligomers and chemically or enzymatically (for example via PCR) amplified nucleobase sequences containing compounds. Microbiological entities in connection with this invention are understood to include cells, for example from animals, vertebrates, bacterial or plants, or viruses, like HIV or HBV, plasmids or genomes.

In these analytical methods, the formation of the triplex structure having the further PNA oligomer incorporated is taken as an indication of the presence of the entity in the sample analyzed, for example the sample containing the chemical or microbiological entity.

The present invention also provides methods for sequence-specific recognition of a double-stranded polynucleotide, comprising contacting said polynucleotide with a compound of Formula I or II.

The present invention further provides methods for sequence-specific recognition of a double-stranded polynucleotide, comprising contacting the polynucleotide with an oligomeric compound that binds to the polynucleotide to form a triplex structure, the oligomeric compound comprising a monomeric unit having the Formula I or II.

Additional advantages and novel features of this invention will become apparent to those skilled in the art upon examination of the examples thereof provided below, which should not be construed as limiting the appended claims.

EXAMPLES

The synthesis of Compound II through V are summarized in Scheme 1 below:

Scheme I

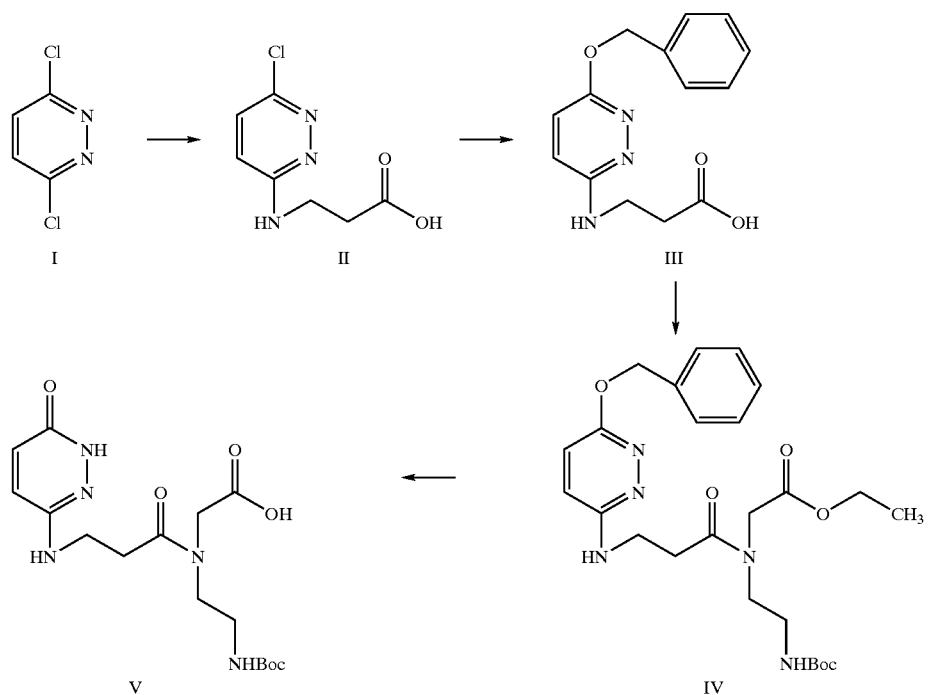

Example 1

N-(3-Chloropyridazin-6-yl)-3-aminopropionic Acid (Compound II)

To a solution of 3,6-dichloropyridazine (50.0 mmol, 7.45 g) and 3-aminopropionic acid (60.0 mmol, 5.34 g) in absolute ethanol (20 mL) was added potassium carbonate (30.0 mmol, 4.15 g), and the suspension was heated to reflux for 3 hours. The mixture was allowed to cool to room temperature, and the light brown solid residue was partitioned between ethyl acetate (300 mL) and water (300 mL). The pH of the aqueous phase was adjusted to 3.5 with 2M aqueous hydrochloric acid, and the yellow solid was filtered and washed with absolute ethanol (10 mL) and diethyl ether (2×20 mL) to give 5.04 g (50%). The product was pure according to TLC Rf 0.31 (dichloromethane/methanol/acetic acid, 85:10:5).

Mp 217–218° C. (decomposed); $^1$H NMR (DMSO-$d_6$): δ 12.24 (bs, 1H, COOH), 7.34 (d, J=9.0 Hz, 1H, aromatic), 7.22 (m, 1H, NH), 6.92 (d, J=9.0 Hz, 1H, aromatic), 3.51 (q, J=6.6 Hz, 2H, ($CH_2$)N), 2.63 (t, J=6.6 Hz, 2H, ($CH_2$)C(O)). $^{13}$C NMR (DMSO-$d_6$): δ 173.08, 158.18, 145.31, 128.59, 118.58, 36.99, 33.34.

Example 2

N-(3-Benzyloxypyridazin-6-yl)-3-aminopropionic Acid (Compound III)

Sodium hydride (22.0 mmol, 0.88 g) was dissolved in benzyl alcohol (10 mL). To the resulting solution was added N-(3-chloropyridazin-6-yl)-3-aminopropionic acid (10.0 mmol, 2.01 g), and the mixture was heated to about 165° C. (oil bath 180° C.) for 3 hours. After cooling to room temperature, water (120 mL) was added, and the aqueous phase was extracted with dichloromethane (3×50 mL). The pH was adjusted to 4.0 with 2M aqueous hydrochloric acid. The light brown precipitate was filtered, washed with water (2×1 mL) and dried over phosphorus pentoxide. The resulting solid was dried to give 1.36 g (47%) of the title compound. The product was pure according to TLC Rf 0.16 (dichloromethane/methanol/acetic acid, 85:10:5).

Mp 258–259° C.; $^1$H NMR (DMSO-$d_6$): δ 12.21 (bs, 1H, COOH), 7.5–7.3 (m, 5H, aromatic), 6.93 (d, J=9.3 Hz, 1H, aromatic), 6.89 (d, J=9.3 Hz, 1H, aromatic), 6.54 (m, 1H, NH), 5.32 (s, 2H, $CH_2$—Ph), 3.47 (t, J=6.6 Hz, 2H, ($CH_2$)N), 2.63 (t, J=6.6 Hz, 2H, ($CH_2$)C(O)); $^{13}$C NMR (DMSO-d6): δ 173.39, 158.60, 156.07, 137.41, 128.39, 128.04, 127.80, 120.71, 119,34, 67.40, 37.25, 33.64; FAB+: 274.1 (M+1).

Example 3

Ethyl N-(2-Boc-aminoethyl)-N-[N'-{(3-benzyloxy) pyridazine-6-yl}-3-aminopropionyl]glycinate (Compound IV)

Ethyl N-(2-Boc-aminoethyl)glycinate (1.80 mmol, 444 mg) was dissolved in dimethyl formamide (12 mL), N-(3-benzyloxypyridazin-6-yl)-3-aminopropionic acid (1.98 mmol, 542 mg) and 3-hydroxy-1,2,3-benzotriazine-4(3H)-one (2.0 mmol, 326 mg) were added. The mixture was cooled in an ice bath, and N,N'-dicyclohexyl-carbodiimide (2.2 mmol, 454 mg) was added. After 1 hour, the ice bath was removed, and the mixture was stirred overnight at room temperature. The mixture was evaporated under vacuum, redissolved in dichloromethane (40 mL) and washed with 5-percent aqueous sodium bicarbonate (2×20 mL). Acetonitrile (10 mL) was added, and the organic phase was evaporated under vacuum. The crude product was purified on a silica column eluted with dichloromethane/methanol (97:3). Fractions containing the product were pooled and evaporated under vacuum to give 0.704 g (78%) of the title compound. The product was pure according to TLC Rf 0.41 (dichloromethane/ methanol, 90:10).

$^1$H NMR (CDCl$_3$): δ 7.5–7.3 (m, 5H, aromatic), 6.79 (d, J=9.3 Hz, 1H, aromatic), 6.71 (d, J=9.3 Hz, 1H, aromatic), 5.72 (m, 1H, NH), 5.40 (s, 2H, $CH_2$—Ph), 5.31 (m, 1H, NH), 4.19 (q, J=7.1 Hz, 2H, $CH_2$), 4.01 & 4.06 (s, 2H, O($CH_2$)—Ph), 3.78 (m, 2H, $CH_2$), 3.50 (m, 2H, $CH_2$), 3.26 (m, 2H, $CH_2$), 2.76 & 2.60 (m, 2H, $CH_2$), 1.41 & 1.39(s, 9H, Boc); $^{13}$C NMR (CDCl$_3$): δ 173.30 (mi.) & 173.07 (ma.), 170.01, 169.50, 159.34, 155.99 (mi) & 155.70 (ma.), 137.05, 128.40, 128.18, 127.89, 120.70, 119.94, 79.42, 68.37 (ma.) & 68.27 (mi.), 61.76 (mi.) & 61.36 (ma.), 50.49 (mi.) & 49.24 (ma.), 48.75 (ma.) & 47.60 (mi.), 38.96 (ma.) & 38.77 (mi.), 37.80 (mi.) & 37.50 (ma.), 32.05 (mi.) & 31.93 (ma.), 28.36, 14.11; FAB+: 502.3 (M+1).

Example 4

N-(2-Boc-aminoethyl)-N-[N'-(3-oxo-2,3-dihydropyridazin-6yl)-3-aminopropionyl]glycine (Compound V)

Ethyl N-(2-Boc-aminoethyl)-N-[N'-((3-benzyloxy) pyridazine-6-yl)-3-aminopropionyl]glycinate (0.88 mmol, 440 mg) was suspended in tetrahydrofuran (4.25 mL). The suspension was cooled, and 1M aqueous lithium hydroxide (2.5 mL) was added. After 30 minutes, dichloromethane (6 mL) was added, and the organic phase was extracted with water (6 mL). The pH of the aqueous phase was adjusted to 4.0 by the dropwise addition 2M aqueous hydrochloric acid, and the aqueous phase was extracted with dichloroethane (6 mL). The organic phase was evaporated under vacuum, and redissolved in absolute ethanol (30 mL), and a palladium/carbon catalyst (240 mg) was added. The mixture was hydrogenated for 2 hours and the catalyst was filtered off. The resulting solution was concentrated under reduced pressure then dried under high vacuum to give 333 mg (80%) of the title compound. The product was pure according to TLC Rf 0.07 (dichloromethane/methanol, 80:20).

$^1$H NMR (acetone-$d_6$): δ 7.09 (d, J=9.9 Hz, 1H, aromatic), 6.75 (d, J=9.9 Hz, 1H, aromatic), 6.22 & 6.06 (m, 1H, NH), 5.75 (m, 1H, NH), 4.23 & 4.10 (m, 2H, $CH_2$), 3.46 (m, 2H, $CH_2$), 3.28 & 3.23 (m, 2H, $CH_2$), 2.78 & 2.58 (m, 2H, $CH_2$), 1.39 & 1.38 (s, 9H, Boc); FAB+: 384.1 (M+1).

Example 5

Evaluation of Specificity of 3-oxo-2,3-Dihydropyridazine for Thymidine (T-A Base Pair) in a Nucleic Acid Target The synthesis of PNA oligomers including bis-PNA were carried out as illustrated in Egholm, et al., *J. Am. Chem. Soc.*, 1992, 114, 1895–1897 & 9677–9678 also see published PCT Application WO 96/02558 entitled Linked Peptide Nucleic Acids.

To determine the specificity for thymidine in an oligodeoxynucleotide by a PNA oligomer having a 3-oxo-2,3-dihydropyridazine group, a 16-mer oligodeoxynucleotide containing a 10-mer target sequence was prepared and treated with three bis-PNA's having varying groups at two positions of the Hoogsteen strand. The bis-PNA's were prepared having two 10-mer PNA's joined via three consecutive 8-amino-3,6-dioxaoctanoic acid groups (egl). The two 10-mers were joined anti-parallel as shown below. Positions that would normally have a protonated cytosine (as determined by the target sequence) in the Hoogsteen strand are occupied by pseudoisocytosine (J).

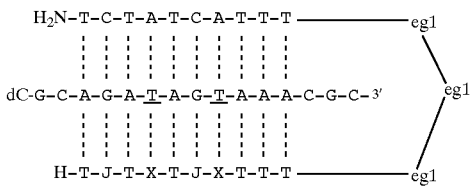

The three bis-PNA's differed only with respect to the groups designated by the variable X in the figure above. The binding of each bis-PNA was measured on a solution ca. 3 $\mu$M in PNA and DNA at pH 7.0 in 100 mM NaCl, 10 mM sodium phosphate, 0.1 mM EDTA. Absorption at 260 nm were recorded with 0.5° C. intervals from 5–90° C.

| SEQ ID No. | Oligonucleotide target sequence |
|---|---|
| 1 | 5'-dCGC AGA TAG TAA ACG C -3' |
| SEQ ID No. | Bis-PNA (Tm in ° C.) |
| 2 | X = 3-oxo-2,3-dihydropyridazine (57.0) |
| 3 | X = N-acetyl-N-(2-aminoethyl) glycine (47.5) |
| 4 | X = Guanine (46.0) |

The N-acetyl-N-(2-aminoethyl)glycine group is a null position having no base attached to the backbone. The N-acetyl-N-(2-aminoethyl)glycine group cannot stack or form hydrogen bonds to thymine. Guanine was used as a comparison as it has been reported that guanine interacts with thymine (T) to form fairly stable G:T-A triplets in DNA triple helices (see Best, et al., *J. Am. Chem. Soc.*, 1995, 117, 1187–1193.

The increased Tm is believed to be due to the increased specificity for the thymidine by the 3-oxo-2,3-dihydropyridazine. The increase is considerably higher than that of guanine.

Example 6

Evaluation of Specificity of 3-oxo-2,3-Dihydropyridazine for Cytidine (C-G Base Pair) in a Nucleic Acid Target The synthesis of PNA oligomers including bis-PNA were carried out as illustrated in Egholm, et al., *J. Am. Chem. Soc.*, 1992, 114, 1895–1897 & 9677–9678 also see published PCT Application WO 96/02558 entitled Linked Peptide Nucleic Acids.

To determine the specificity for cytidine in an oligodeoxynucleotide by a PNA oligomer having a 3-oxo-2,3-dihydropyridazine group, a 16-mer oligodeoxynucleotide containing a 10-mer target sequence was prepared and treated with three bis-PNA's having varying groups at two positions of the Hoogsteen strand. The bis-PNA's were prepared having two 10-mer PNA's joined via three consecutive 8-amino-3,6-dioxaoctanoic acid (egl) groups. The two 10-mers were joined in anti-parallel orientation as shown below. Positions that would normally have a protonated cytosine (as determined by the target sequence) in the Hoogsteen strand are occupied by pseudoisocytosine (represented as "J").

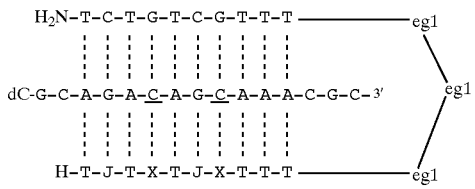

The three bis-PNA's differed only with respect to the groups designated by the variable X in the structure shown above. The binding of each bis-PNA was measured on a solution ca. 3 $\mu$M in PNA and DNA at pH 7.0 in 100 mM NaCl, 10 mM sodium phosphate, 0.1 mM EDTA. Absorption at 260 nm were recorded with 0.5° C. intervals from 5–90° C.

| SEQ ID No. | Oligonucleotide target sequence |
|---|---|
| 5 | 5'-dCGC AGA CAG CAA ACG C -3' |
| SEQ ID No. | Bis-PNA (Tm in ° C.) |
| 6 | X = 3-oxo-2,3-dihydropyridazine (42.0; 48.0) |
| 7 | X = N-acetyl-N-(2-aminoethyl)glycine (62.0) |
| 8 | X = Cytidine (61.5) |

The N-acetyl-N-(2-aminoethyl)glycine group is a null position having no base attached to the backbone. The N-acetyl-N-(2-aminoethyl)glycine group cannot stack or form hydrogen bonds to cytidine.

The 3-oxo-2,3-dihydropyridazine was incorporated next to the C-G base pair and compared to a null group and to a cytidine group to see if the increased specificity seen with thymidine (57° C. vs. 47° C. for the null base, Example 5) is seen for cytidine. The effect with cytidine as seen by the large drop in the Tm was destabilizing for the triplex structure. The null base (X=N-acetyl-N-(2-aminoethyl) glycine) and the guanidine group show about the same effect; neither appear to be significantly stabilizing or destabilizing relative to the other.

Example 7

Evaluation of Binding of SEQ ID No. 2 to Nucleic Acid Targets

The binding of a bis PNA (SEQ ID No. 2, Example 5) to 8 different oligodeoxynucleotide target sequences was measured following the procedures illustrated in Example 5. The positions on the oligodeoxynucleotide target sequences that are complementary the two 3-oxo-2,3-dihydropyridazine (hereinafter "ODHP") groups are varied in order to see the effect of a mismatch on the specificity. The target sequences and the resulting Tm's of the triple helix structures formed are shown below.

| SEQ ID No. | Oligodeoxynucleotide target | Tm(° C.) |
|---|---|---|
| 9 | 5'-dCGC AGA TAG TAA ACG C-3' | 57.0 |
| 10 | 5'-dCGC AGA AAG TAA ACG C-3' | 45.0 |

25
-continued

| SEQ ID No. | Oligodeoxynucleotide target | Tm(° C.) |
|---|---|---|
| 11 | 5'-dCGC AGA GAG TAA ACG C-3' | 40.0 |
| 12 | 5'-dCGC AGA CAG TAA ACG C-3' | 40.0 |
| 13 | 5'-dCGC AGA UAG UAA ACG C-3' | 63.5 |
| 14 | 5'-dCGC AGA AAG UAA ACG C-3' | 49.5 |
| 15 | 5'-dCGC AGA GAG UAA ACG C-3' | 44.5 |
| 16 | 5'-dCGC AGA CAG UAA ACG C-3' | 44.5 |

The formation of the ODHP.T-A triplet proved to be highly specific, as indicated by the dramatic decrease in thermal stability when ODHP was positioned opposite to either adenine, guanine or cytosine. The differences in melt temperatures per mismatch (δ Tm per mismatch) relative to thymine (T) control were 12° C. for A; 16.5° C. for G; and 12.0° C. for C. The increased Tm with SEQ ID #13 (which has uracil at both variable positions) is believed to reflect interference from the methyl group present in thymine.

Example 8

Evaluation of Binding of SEQ ID No. 6 to Nucleic Acid Targets

The binding of SEQ ID No. 6 to four different oligodeoxynucleotide target sequences was measured according to the procedures described in Example 5. The positions on the oligodeoxynucleotide target sequences that are complementary to the two 3-oxo-2,3-dihydropyridazine groups were varied in order to see the effect of a mismatch on the specificity. The target sequences and the resulting Tm's of the triple helix structures formed are shown below.

| SEQ ID No. | Oligodeoxynucleotide target | Tm(° C.) |
|---|---|---|
| 17 | 5'-dCGC AGA CAG CAA ACG C-3' | 42.0;48.0 |
| 18 | 5'-dCGC AGA AAG CAA ACG C-3' | 50.0 |
| 19 | 5'-dCGC AGA GAG CAA ACG C-3' | 50.0 |
| 20 | 5'-dCGC AGA TAG CAA ACG C-3' | 51.0 |

When the 3-oxo-2,3-dihydropyridazine groups are interacting with C-G base pairs there is a strong destabilizing effect as seen by the Tm. This effect is not seen with either the null base, or with the cytidine group in the position complementary to the C-G base pair.

The synthesis of monomer synthons having the formulas VI–VII (Examples 9–15) is shown below:

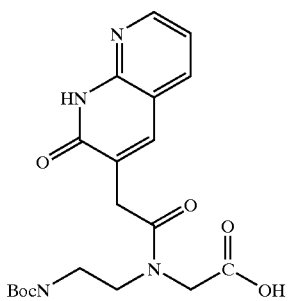

VI

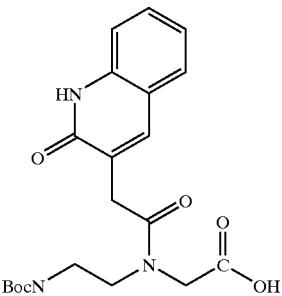

VII

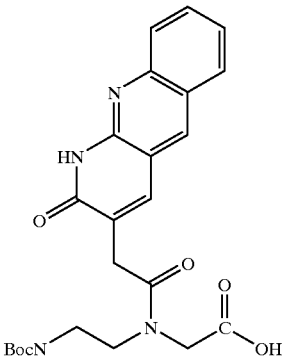

VIII

Example 9

[1,8]Napthyridin-2(1H)-one 3-Acetic Acid

To a solution of THF (30 mL) and LDA (24.4 mmol), cooled to −78° C., was slowly added a solution of di-t-butyl succinate (5.60 g) in THF (4.0 mL). After 15 minutes 3-carbaldehyde-2-pivaloylaminopyridine (2.37 g) dissolved in THF (7 mL) was added. The clear yellow solution was stirred at −78° C. for 15 minutes and then allowed to warm to room temperature. The solution was then poured into saturated aqueous ammonium chloride (200 mL) and extracted with dichloromethane (2×100 mL). The organic phase was dried ($Na_2SO_4$) and evaporated in vacuo. A solution of the diastereomeric alcohols in a 3:1 mixture of 3M aqueous HCl:THF was heated to reflux for 24 hours. After cooling to room temperature the pH was adjusted to 4 and the resulting solid filtered and dried under vacuum to give 1.52 g (65%) of the title compound as a tan colored material.

$^1$H NMR (DMSO-$d_6$): δ 12.19 (bs, 1H, NH), 8.48 (dd, j=4.8, 1.8, 1H), 8.09 (dd, j=7.7, 1.8, 1H), 7.86 (s, 1H), 7.24 (dd, 7.7, 4.7, 1H), 3.48 (s, 2H).

Example 10

Methyl N-(2-Boc-aminoethyl)-N-([1,8]napthyridin-2 (1H)-on-3-yl)acetyl)glycinate Methyl N-(2-Boc-aminoethyl)glycinate (4.50 mmol) was dissolved in DMF (20 mL) and [1,8]napthyridin-2(1H)-one 3-acetic acid (1.02 g, 5.00 mmol), HOAt (0.68 mL, 5.00 mmol) and DIEA (0.871 mL, 5.0 mmol) were added. After cooling to 0° C. DCC (1.13 g, 5.5 mmol) was added. After 1 hour the ice bath was removed and the mixture was stirred overnight at room temperature. The mixture was evaporated in vacuo, redissolved in ethyl acetate (150 mL) and washed with saturated aqueous $NaHCO_3$ (2×50 mL) followed by water (50 mL). The organic phase was dried ($MgSO_4$) and evaporated in vacuo. The crude product was purified on a silica column eluted with dichloromethane/methanol (9:1, v/v). Fractions containing product were pooled and evaporated in vacuo to give 1.09 g (58%) of the title compound as a tan solid.

$^1$H NMR (DMSO-d$_6$): δ 12.18 (bs, 1H, NH), 8.49–8.47 (m, 1H, aromatic), 7.79–7.76 (s, 1H, aromatic), 7.25–7.22 (m, 1H, aromatic), 6.91–6.75 (t, 1H, NH), 4.37–4.06 (s, 2H, CH$_2$), 3.67–3.48 (s, 2H, CH$_2$), 3.64 (s, 3H, CH$_3$O), 3.49–3.46 (m, 2H, CH$_2$), 3.20–3.15 (m, 2H, CH$_2$), 1.36–1.35 (s, 9H, CH$_3$, (Boc)). $^{13}$C NMR (DMSO-D$_6$): δ 170.32 (170.54), 170.10, 162.61, 155.83, 149.86, 149.31, 136.52 (136.83), 135.87 (135.99), 129.94 (129.64), 118.46, 114.44, 78.05 (77.81), 51.83 (52.21), 48.19, 47.64 (46.69), 38.46 (38.00), 33.49 (33.82), 28.28. FAB$^+$ MS: 419.22 (M+H$^+$, calc. For C$_{20}$H$_{26}$N$_4$O$_6$+H$^+$ 419.19).

Example 11

N-(2-Boc-aminoethyl)-N-([1,8]napthyridin-2(1H)-on-3-yl)acetyl)glycine (Compound VI)

To a solution of methyl N-(2-Boc-aminoethyl)-N-([1,8] napthyridin-2(1H)-on-3-yl)acetyl)glycinate was added 2M aqueous LiOH (6.0 mL, 12.0 mmol). After 20 minutes at room temperature additional water (15 mL) was added and the THF was removed in vacuo. The pH of the aqueous phase was adjusted to 3.0 by addition of 2M HCl. The precipitate was filtered off, washed with water (2×10 mL) and dried in vacuo to give 852 mg (88%) of the title compound as a colorless powder.

$^1$H NMR (DMSO-d$_6$): δ 12.67 (bs, 1H, COOH), 12.20 (BS, 1H, NH), 8.49–8.46 (m, 1H, aromatic), 7.82–7.76 (s, 1H, aromatic), 7.26–7.22 (m, 1H, aromatic), 6.91–6.74 (t, 1H, NH), 4.25–3.98 (s, 2H, CH$_2$), 3.61–3.47 (s, 2H, CH$_2$), 3.47–3.40 (m, 2H, CH$_2$), 3.22–3.02 (m, 2H, CH$_2$), 1.36–1.35 (s, 9H, CH$_3$, (Boc)). $^{13}$C NMR (DMSO-D$_6$): δ 172.58 (172.38), 170.50 (170.14), 162.70, 156.71, 155.75, 155.02, 153.29, 149.89, 136.08, 128.54, 128.20, 128.00, 9391, 77.95, 66.49, 52.18 (51.70), 49.65 (49.32), 47.59 (47.37), 33.42, 31.80 (31.42), 28.24 (28.06), 25.40 (24.53), 21.66. FAB$^+$ MS: 405.18 (M+H$^+$, calc. For C$_{19}$H$_{24}$N$_4$O$_6$+H$^+$ 405.18).

Example 12

3-Formyl-2-pivaloylaminoquinoline

To a solution of 2-pivaloylaminoquinoline (5.00 g, 21.92 mmol) in THF (75 mL) at –78° C. was added dropwise BuLi (5.48 mL, 10 M in hexane, 54.80 mmol). After 2 hours at –78° C. the dianion was quenched by the addition of N-formylmorpholine (3.79 g, 37.88 mmol). The reaction mixture was allowed to warm to room temperature and poured into 2M aqueous HCl (20 mL). The pH of the aqueous phase was adjusted to 7.0 by addition of 2M HCl and the aqueous phase was diluted with water (100 mL) and extracted with diethyl ether (2×100 mL). The organic phase was dried (MgSO$_4$) and evaporated to dryness in vacuo. The crude product was recrystallized from petrol ether/ethyl acetate to give 2.92 g (52%) of the title compound.

$^1$H NMR (DMSO-d$_6$): δ 10.70 (bs, 1H, NH), 9.82 (s, 1H, CHO), 8.85 (s, 1H, aromatic), 8.19–8.17 (m, 1H, aromatic), 7.97–7.95 (m, 1H, aromatic), 7.91–7.87 (m, 1H, aromatic), 7.76–7.62 (m, 1H, aromatic), 1.30 (s, 9H, CH$_3$). $^{13}$C NMR (DMSO-D$_6$): δ 189.62, 189.55, 178.37, 149.66, 148.15, 140.33, 132.77, 129.82, 127.51, 126.59, 125.48, 123.64, 26.97. FAB$^+$ MS: 257.05 (M+1, calc. For C$_{15}$H$_{16}$N$_2$O$_2$+H$^+$ 257.13) and 279.04 (M+Na$^+$, calc. for C$_{15}$H$_{16}$N$_2$O$_2$+Na$^+$ 279.11).

Example 13

Benzo[b][1,8]napthyridin-2(1H)-one 3 Acetic Acid

To absolution of THF (15 mL) and LDA(2M in THF, 15.9 mmol, 7.95 mL), cooled to –78° C., was slowly added a solution of di-t-butyl succinate (15.9 mmol, 3.28 g) in THF (3.0 mL). After 15 minutes at –78° C. 3-Formyl-2-pivaloylaminoquinoline (1.92 g, 7.50 mmol) dissolved in THF (10 mL) was added. The clear yellow solution was stirred at –78° C. for 15 minutes and then allowed to warm to room temperature. The solution was poured into saturated aqueous ammonium chloride (200 mL) and extracted with dichloromethane (2×100 mL). The organic phase was dried (MgSO$_4$) and evaporated in vacuo. The crude product of diastereomeric alcohols was heated to reflux for 24 hours in a mixture of THF (5 mL) and HCl (3M, aqueous) and then poured into water (100 mL) and neutralized with K$_2$CO$_3$. The tan precipitate was washed with water (2×25 mL) and dried in vacuo overnight. The crude product (1.60 g) was heated in acetonitrile (50 mL) and filtered while hot. The product was washed with ether (2×25 mL) and dried in vacuo to give 1.50 g (79%) of a material judged to be 61% pure according to HPLC (260 nm).

Example 14

Methyl N-(Benzo[b][1,8]napthyridin-2(1H)-one 3-yl)-N-(2-boc-aminoethyl)glycinate Methyl N-(2-Boc-aminoethyl)glycinate (0.812 g, 3.5 mmol) was dissolved in DMF (10 mL) and benzo[b][1,8] napthyridin-2(1H)-one 3 acetic acid (883 mg, 3.5 mmol) was added. The mixture was cooled in an ice bath and HBTU (1.52 g, 4.0 mmol) was added. After 1 hour the ice bath was removed and the mixture was stirred overnight at room temperature. The mixture was evaporated in vacuo, redissolved in dichloromethane (100 mL) and washed with saturated aqueous NaHCO$_3$ (2×50 mL). The organic phase was dried (MgSO$_4$) and evaporated in vacuo. The crude product was purified on a silica column eluted with dichloromethane/methanol (97:3, v/v). Fractions containing the product were pooled and evaporated in vacuo to give 345 mg (21%) of the title compound as a tan solid.

$^1$H NMR (DMSO-d$_6$): δ 12.13 (bs, 1H, NH), 8.70–8.65 (m, 1H, aromatic), 7.91 (s, 1H, aromatic), 7.88 (s, 1H, aromatic), 7.79–7.75 (m, 1H, aromatic), 7.55–7.49 (m, 1H, aromatic), 6.90–6.72 (bs, 1H, NH), 4.36–4.05 (s, 2H, CH$_2$), 4.11 (q, J=, 2H, CH$_2$), 3.67–3.33 (s, 2H, CH$_2$), 3.48–3.53 (m, 2H, CH$_2$), 3.27–3.04 (m, 2H, CH$_2$), 1.35 (s, 9H, CH$_3$ (Boc)). $^{13}$C NMR (DMSO-D$_6$): δ 170.17 (170.32), 170.01 (170.39), 163.08 (163.17), 155.75 (155.63), 148.67, 147.02, 136.20 (136.46), 136.07 (136.13), 131.17, 130.16 (129.88), 128.67, 126.90, 124.85 (124.67), 115.67 (115.63), 78.00 (77.76), 51.81 (52.20), 48.18 (48.38), 47.63, 38.43 (38.29), 33.56 (33.87), 28.26. FAB$^+$ MS: 469.10 (M+H$^+$, calc. For C$_{24}$H$_{28}$N$_4$O$_6$+H$^+$ 469.21).

Example 15

N-(Benzo[b][1,8]napthyridin-2(1H)-on-3-yl)acetyl)-N-(2-boc-aminoethyl)glycine (Compound VIII)

To a solution of Methyl N-(benzo[b][1,8]napthyridin-2 (1H)-one 3-yl)-N-(2-Boc-aminoethyl)glycinate (0.426 mmol, 200 mg) in THF (4.0 mL) was added 2M aqueous (1.07 mL, 2.14 mmol). After 15 minutes at room temperature additional water (7.0 mL) was added and the THF was removed in vacuo. The aqueous phase was extracted with dichloromethane (2×2 mL) and the pH was adjusted to 3.0 by the addition of 2M aqueous HCl. The precipitate formed was filtered off, washed with water (2×5 mL) and dried in vacuo to give 176 mg (91%) of the title compound as a tan powder.

FAB$^-$ MS: 453.42 (M–H$^+$, calc. For C$_{34}$H$_{26}$N$_4$O$_6$–H$^+$ 453.18).

Example 16

Methyl N-(2-Boc-aminoethyl)-N-(quinolin-2(1H)-on-3-yl)acetyl)glycinate

Ethyl N-(2-Boc-aminoethyl)glycinate (443 mg, 1.8 mmol) was dissolved in DMF (10 mL) and quinolin-2(1H)- one-3-acetic acid (prepared as per the procedure of Shanmugam, P., Naturforsch, 1973, 196, 551–553) (406 mg, 2.0 mmol) and HOAt (272 mg, 2.0 mmol) was added. The mixture was cooled on ice and DCC (413 g, 2.0 mmol) was added. After 1 hour the ice bath was removed and the mixture was stirred overnight at room temperature. The mixture was evaporated in vacuo, redissolved in ethyl acetate (100 mL) and washed with saturated aqueous $NaHCO_3$ (2×30 mL) followed by water (30 mL). The organic phase was dried ($MgSO_4$) and evaporated in vacuo. The crude product was purified on a silica column eluted with dichloromethane/methanol (9:1, v/v). Fractions containing the product were pooled and evaporated in vacuo to give 476 mg (60%) of the title compound as a tan solid.

Example 17

N-(2-Boc-aminoethyl)-N-(quinolin-2(1H)-on-3-yl)acetyl)-glycine (Compound VII)

To a solution of methyl N-(2-Boc-aminoethyl)-N-(quinolin-2(1H)-on-3-yl)acetyl)glycinate (427 mg, 0.99 mmol) in THF (10 mL) was added 2M aqueous LiOH (2.5 mL, 5 mmol). After 20 minutes at room temperature additional water (10 mL) was added. The THF was evaporated in vacuo and 2M aqueous HCl (2.5 mL) was added with vigorous stirring. The precipitate was filtered off, washed with water (2×10 mL) and dried in vacuo to give 280 mg (74%) of the title compound as a colorless powder.

$^1$H NMR (DMSO-$d_6$): δ 11.77 (bs, 1H, NH), 781 (7.74) (s, 1H, aromatic), 7.64–7.13 (m, 4H, aromatic), 6.95–6.65 (m, 1H, NH), 3.98 (4.25) (s, 2H, $CH_2$), 3.59 (3.45) 3.30–3.00 (m, 4H, 2×$CH_2$), 1.37 (1.35) (s, 9H, $CH_3$ (Boc)).

Example 18

Ethyl N-[(2-Hydroxy-10-H-pyrimido[5,4-b][1,4]benzothiazin-1-yl)acetyl]-N-(2-boc-aminoethyl) glycinate 2-Hydroxy-10-H-pyrimido[5,4-b][1,4]benzothiazin (653 mg, 3.0 mmol) was suspended in DMF (30 mL) and NaH (60% in mineral oil, 132 mg, 3.3 mmol) was added in one portion. After 15 minutes ethyl N-bromoacetyl-N-(2-Boc-aminoethyl)-glycinate (1.10 g, 3.3 mmol) was added. The mixture was stirred at room temperature for 2 hours, evaporated in vacuo, redissolved in dichloromethane (200 mL) and washed once with saturated aqueous $NaHCO_3$ (100 mL) and once with saturated aqueous NaCl. The mixture was dried ($MgSO_4$) and evaporated to dryness in vacuo. The crude material was purified on a silica gel column using methanol/dichloromethane (1:9, v/v) as the eluent to give 853 mg (57%) of the title compound.

$^1$H NMR (DMSO-$d_6$): δ 10.37 (bs, 1H, NH), 7.51 (s, 1H, H-6), 7.09–7.05 (m, 2H, aromatic), 6.94–6.75 (m, 3H, aromatic+NH), 4.66–4.48 (s, 2H, $CH_2$), 4.30–4.04 (s, 2H, $CH_2$), 4.18–4.08 (q, 2H, $CH_2$), 3.41 (m, 2H, $CH_2$), 3.20–3.03 (m, 2H, $CH_2$), 1.38–1.37 (s, 9H, $CH_3$ (Boc)), 1.24–1.18 (t, 3H, $CH_3$) $^{13}$C NMR (DMSO-$D_6$): δ 169.44+169.09, 167.87+167.58, 160.15, 155.82, 154.58, 141.23, 136.50, 127.49, 126.09, 124.01, 116.97, 115.83+115.76, 93.39, 78.13+77.85, 61.22+60.61, 49.26+49.02, 48.01, 47.09, 38.33, 28.25, 14.109. FAB$^+$ MS: 503.18 (M+H$^+$, calc. For $C_{23}H_{29}N_5O_6S+H^+$ 504.19).

Example 19

N-[(2-Hydroxy-10-H-pyrimido[5,4-b][1,4]benzothiazin-1-yl)acetyl]-N-(2-boc-aminoethyl) glycine Ethyl N-[(2-hydroxy-10-H-pyrimido[5,4-b][1,4]benzothiazin-1-yl)acetyl]-N-(2-Boc-aminoethyl)glycinate (201 mg, 0.4 mmol) was dissolved in THF (10 mL) and LiOH (2M, aqueous, 1.0 mL) was added. After 15 minutes at room temperature water (10 mL) was added, the THF was evaporated in vacuo and HCl (2M, aqueous, 1.0 mL) was added with vigorous stirring. The solid yellow material was filtered off and dried in vacuo to give 173 mg (91%) of the title compound.

$^1$H NMR (DMSO-$d_6$): δ 10.37 (bs, 1H, NH), 7.51 (s, 1H, H-6), 7.09–7.05 (m, 2H, aromatic), 6.94–6.75 (m, 3H, aromatic+NH), 4.66–4.48 (s, 2H, $CH_2$), 4.30–4.04 (s, 2H, $CH_2$), 3.41 (m, 2H, $CH_2$), 3.20–3.03 (m, 2H, $CH_2$), 1.38–1.37 (s, 9H, $CH_3$ (Boc)). FAB$^+$ MS: 476.23 (M+H$^+$, calc. For $C_{21}H_{25}N_5O_6S+H^+$ 476.16).

Example 20

Hybridization of PNA 10 mers Having N-(Benzo[b][1,8]napthyridin-2(1H)-on-3-yl)acetyl)-N-(2-boc-aminoethyl)glycine Monomers at Selected Positions to PNA and DNA Target Sequences The hybridization of PNA 10 mers having 0, 1, or 3 tricyclic N-(benzo[b][1,8]napthyridin-2(1H)-on-3-yl)acetyl)-N-(2-Boc-aminoethyl)glycine monomers (Example 15) incorporated at selected positions was measured against both PNA (SEQ ID No. 21) and DNA (SEQ ID No. 22) target sequences. The PNA sequences were prepared as illustrated in Egholm, supra.

The three bis-PNA's differed only with respect to the groups designated by the variable X in Table below. The binding of each bis-PNA was measured in a solution ca. 3 μM in PNA and DNA or PNA and PNA at pH 7.0 in 100 mM NaCl, 10 mm sodium phosphate, 0.1 mM EDTA. Absorption at 260 nm were recorded at 0.5° C. intervals from 5–90° C.

| SEQ ID No. | Target sequence |
|---|---|
| 21 | H-AGT GAT CTA C-Lys-$NH_2$ |
| 22 | 5'-dAGT GAT CTA C-3' |

| SEQ ID No. | PNA SEQUENCE | Tm ° C. vs. SEQ ID 21 | Tm ° C. vs. SEQ ID 22 |
|---|---|---|---|
| 23 | H-GTA GAT CAC T-Lys-$NH_2$ | 68.5 | 51.0 |
| 24 | H-GTA GAX CAC T-Lys-$NH_2$ | 68.0 | 51.0 |
| 25 | H-GXA GAX CAC X-Lys-$NH_2$ | 68.0 | 59.0 |

Each variable X is an incorporated N-(benzo[b][1,8]napthyridin-2(1H)-on-3-yl)acetyl)-N-(2-Boc-aminomethyl) glycine monomer. The effect of N-(benzo[b][1,8]napthyridin-2(1H)-on-3-yl)acetyl)-N-(2-Boc-aminoethyl) glycine monomers in a PNA-PNA duplex is null, e.g. not destabilizing. The effect of the three tricyclic monomers in the PNA oligomer has a significant effect on the interaction with the DNA target resulting in an 8° C. increase in Tm.

It is intended that each of the patents, applications, and printed publications mentioned or referred to in this specification be herein incorporated by reference in their entirety.

As those skilled in the art will appreciate, numerous changes and modifications may be made to the preferred embodiments of the invention without departing from the spirit of the invention. It is intended that all such variations fall within the scope of the invention.

What is claimed is:

1. A oligomeric compound comprising a monomeric unit having the formula:

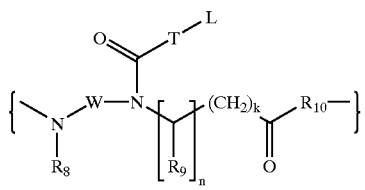

wherein:

$R_8$ is H, COCH$_3$ or an amino protecting group;

$R_9$ is hydrogen or a side chain of a naturally occurring amino acid;

$R_{10}$ is O, NH, O-alkylene or a lysine residue;

W is —(CH2)$_m$— where m is from 0 to 6, or

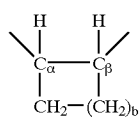

where b is an integer from 0 to 4;

k is from 0 to 5;

n is 0 or 1;

L has the formula

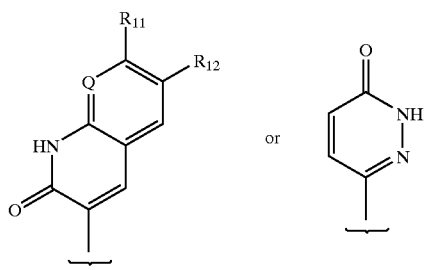

Q is CH or N;

$R_{11}$ and $R_{12}$ are each H;

or $R_{11}$ and $R_{12}$ together with the carbon atoms to which they are attached form a phenyl group;

T has the formula:

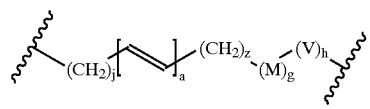

j and z are each, independently, from 0 to 5 with the sum of j and z being from 1 to 7;

M is C(=O), S(O)$_2$, phenyl or P(O)$_2$;

V is NH, S, or CH$_2$; and a, h and g are each, independently, 0 or 1.

2. The compound of claim 1 wherein L has the formula:

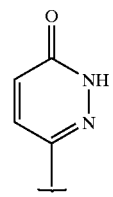

3. The compound of claim 1 wherein L has the formula:

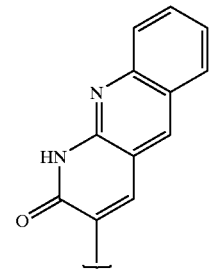

4. The compound of claim 1 wherein L has the formula:

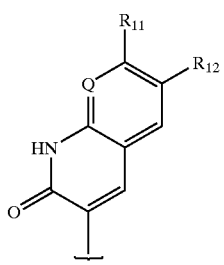

5. The compound of claim 1 wherein $R_{11}$ and $R_{12}$ are each H.

6. The compound of claim 1 wherein $R_{11}$ and $R_{12}$ together with the atoms to which they are attached form a phenyl ring.

7. The compound of claim 1 wherein Q is N.

8. The compound of claim 1 wherein Q is CH.

9. The compound of claim 1 wherein g and h are each 0.

10. The compound of claim 9 wherein a is 0.

11. The compound of claim 1 wherein a is 0, g is 0, V is NH and h is 1.

12. The compound of claim 1 wherein T has the formula —CH$_2$—CH$_2$—NH—.

13. The compound of claim 1 wherein T has the formula —CH$_2$—.

14. The compound of claim 1 wherein T has the formula —CH$_2$—CH$_2$—.

15. The compound of claim 1 wherein W is —(CH$_2$)$_m$—.

16. The compound of claim 15 wherein m is 2.

17. The compound of claim 1 wherein W has the formula:

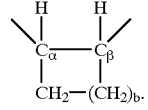

18. The compound of claim 17 wherein b is 2.

19. The compound of claim 17 wherein b is 3.

20. The compound of claim 1 wherein b is 2 or 3.

21. The compound of claim 20 wherein at least one of $C_\alpha$ or $C_\beta$ is in the S configuration.

22. The compound of claim 1 wherein:
$R_8$ is H;
$R_9$ is hydrogen;
$R_{10}$ is O;
W is —$(CH_2)_m$— where m is 2;
k is 1;
n is 0;
L has the formula:

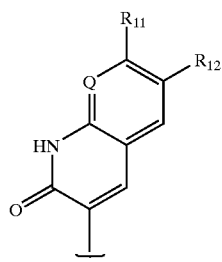

Q is N;

$R_{11}$ and $R_{12}$ together with the carbon atoms to which they are attached form a phenyl group; and T is —$CH_2$—.

23. A compound of formula:

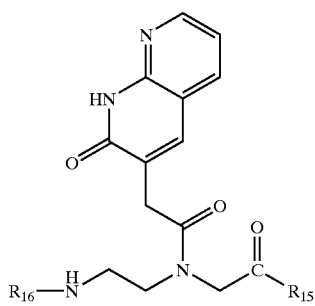

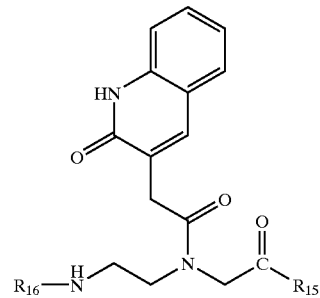

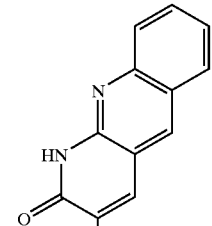

or

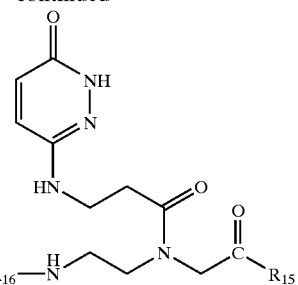

wherein:
$R_{15}$ is OH, a protected hydroxyl group, or a protecting group; and
$R_{16}$ is H or an amino protecting group.

24. A compound consisting of a plurality of peptide nucleic acid oligomers linked by linking groups, wherein at least one of said peptide nucleic acid oligomers comprises a moiety having the formula:

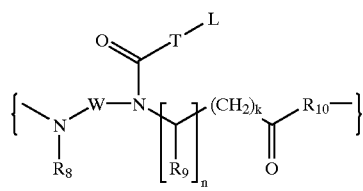

wherein:
$R_8$ is H, $COCH_3$ or an amino protecting group;
$R_9$ is hydrogen or a side chain of a naturally occurring amino acid;
$R_{10}$ is O, NH, O-alkylene or a lysine residue;
W is —$(CH_2)_m$— where m is from 0 to 6, or

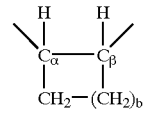

where b is an integer from 0 to 4;
k is from 0 to 5;
n is 0 or 1;
L has the formula

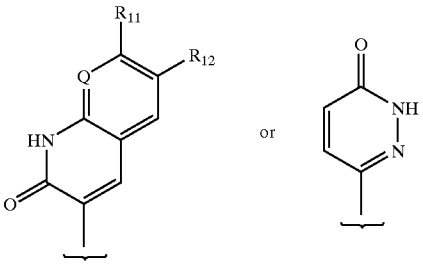

Q is CH or N;
$R_{11}$ and $R_{12}$ are each H;
or $R_{11}$ and $R_{12}$ together with the carbon atoms to which they are attached form a phenyl group;

T has the formula:

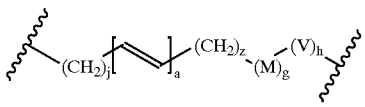

j and z are each, independently, from 0 to 5 with the sum of j and z being from 1 to 7;
M is C(=O), S(O)$_2$, phenyl or P(O)$_2$;
V is NH, S, or CH$_2$; and
a, h and g are each, independently, 0 or 1.

25. The compound of claim 24 wherein two peptide nucleic acid oligomers are linked by a linking group.

26. The compound of claim 24 wherein said linking group is 8-amino-3,6-dioxaoctanoic acid.

27. A compound having the formula:

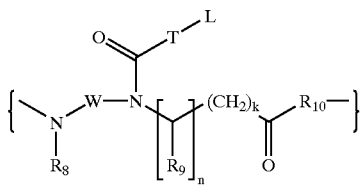

wherein:

$R_8$ is H, COCH$_3$ or an amino protecting group;

$R_9$ is hydrogen or a side chain of a naturally occurring amino acid;

$R_{10}$ is O, NH, O-alkylene or a lysine residue;

W is —(CH$_2$)$_m$— where m is from 0 to 6, or

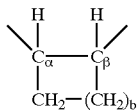

where b is an integer from 0 to 4;
k is from 0 to 5;
n is 0 or 1;
L has the formula

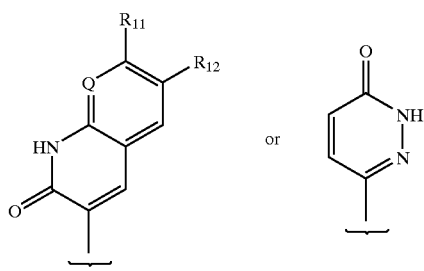

Q is CH or N;
$R_{11}$ and $R_{12}$ are each H;
or $R_{11}$ and $R_{12}$ together with the carbon atoms to which they are attached form a phenyl group;

T has the formula:

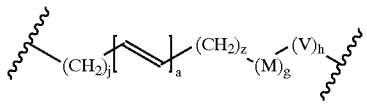

j and z are each, independently, from 0 to 5 with the sum of j and z being from 1 to 7;
M is C(=O), S(O)$_2$, phenyl or P(O)$_2$;
V is NH, S, or CH$_2$; and
a, h and g are each independently 0 or 1; and
$R_{13}$ and $R_{14}$ are each independently H or an amino or carboxyl protecting group.

28. The compound of claim 27 wherein L has the formula:

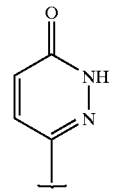

29. The compound of claim 27 wherein L has the formula:

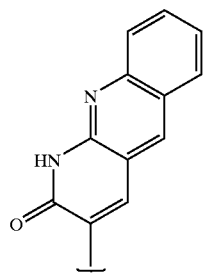

30. The compound of claim 27 wherein L has the formula:

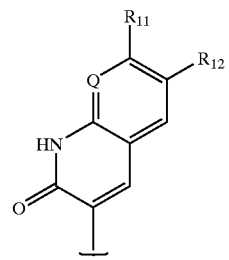

31. The compound of claim 27 wherein $R_{11}$ and $R_{12}$ together with the atoms to which they are attached form a phenyl ring.

32. The compound of claim 27 wherein Q is N.

33. The compound of claim 27 wherein Q is CH.

34. The compound of claim 27 wherein g and h are each 0.

35. The compound of claim 27 wherein a is 0.

36. The compound of claim 27 wherein a is 0, g is 0, X is NH and h is 1.

37. The compound of claim 27 wherein T has the formula —CH$_2$—CH$_2$—NH—.

38. The compound of claim 27 wherein T has the formula —CH$_2$—.

39. The compound of claim 27 wherein T has the formula —CH$_2$—CH$_2$—.

40. The compound of claim 27 wherein b is 2 or 3.

41. The compound of claim 40 wherein at least one of $C_\alpha$ or $C_\beta$ is in the S configuration.

* * * * *

SEQUENCE LISTING

```
<160> NUMBER OF SEQ ID NOS: 25

<210> SEQ ID NO 1
<211> LENGTH: 16
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 1
cgcagatagt aaacgc                                                    16

<210> SEQ ID NO 2
<211> LENGTH: 13
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (10)..(11)
<223> OTHER INFORMATION: Bases 10 and 11 are linked via three
      consecutive 8-amino-3, 6-dioxaoctanoic acid groups (egl)

<400> SEQUENCE: 2
tctatcattt ttt                                                       13

<210> SEQ ID NO 3
<211> LENGTH: 13
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (10)..(11)
<223> OTHER INFORMATION: Bases 10 and 11 are linked via three
      consecutive 8-amino-3, 6-dioxaoctanoic acid groups (egl)

<400> SEQUENCE: 3
tctatcattt ttt                                                       13

<210> SEQ ID NO 4
<211> LENGTH: 13
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (10)..(11)
<223> OTHER INFORMATION: Bases 10 and 11 are linked via three
      consecutive 8-amino-3, 6-dioxaoctanoic acid groups (egl)

<400> SEQUENCE: 4
tctatcattt ttt                                                       13
```

```
<210> SEQ ID NO 5
<211> LENGTH: 16
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 5
cgcagacagc aaacgc                                                    16

<210> SEQ ID NO 6
<211> LENGTH: 13
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (10)..(11)
<223> OTHER INFORMATION: Bases 10 and 11 are linked via three
      consecutive 8-amino-3, 6-dioxaoctanoic acid groups (egl)

<400> SEQUENCE: 6
tctgtcgttt ttt                                                       13

<210> SEQ ID NO 7
<211> LENGTH: 13
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (10)..(11)
<223> OTHER INFORMATION: Bases 10 and 11 are linked via three
      consecutive 8-amino-3, 6-dioxaoctanoic acid groups (egl)

<400> SEQUENCE: 7
tctgtcgttt ttt                                                       13

<210> SEQ ID NO 8
<211> LENGTH: 13
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (10)..(11)
<223> OTHER INFORMATION: Bases 10 and 11 are linked via three
      consecutive 8-amino-3, 6-dioxaoctanoic acid groups (egl)

<400> SEQUENCE: 8
tctgtcgttt ttt                                                       13

<210> SEQ ID NO 9
<211> LENGTH: 16
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 9
cgcagatagt aaacgc                                                    16

<210> SEQ ID NO 10
```

```
<211> LENGTH: 16
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 10
cgcagaaagt aaacgc                                                    16

<210> SEQ ID NO 11
<211> LENGTH: 16
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 11
cgcagagagt aaacgc                                                    16

<210> SEQ ID NO 12
<211> LENGTH: 16
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 12
cgcagacagt aaacgc                                                    16

<210> SEQ ID NO 13
<211> LENGTH: 16
<212> TYPE: DNA
<213> ORGANISM: Artificial Sequence
<220> FEATURE:
<223> OTHER INFORMATION: Description of Combined DNA/RNA Molecule:
      Oligonucleotide
<223> OTHER INFORMATION: Description of Artificial Sequence: Novel
      Sequence

<400> SEQUENCE: 13
cgcagauagu aaacgc                                                    16

<210> SEQ ID NO 14
<211> LENGTH: 16
<212> TYPE: DNA
<213> ORGANISM: Artificial Sequence
<220> FEATURE:
<223> OTHER INFORMATION: Description of Combined DNA/RNA Molecule:
      Oligonucleotide
<223> OTHER INFORMATION: Description of Artificial Sequence: Novel
      Sequence

<400> SEQUENCE: 14
cgcagaaagu aaacgc                                                    16

<210> SEQ ID NO 15
<211> LENGTH: 16
<212> TYPE: DNA
<213> ORGANISM: Artificial Sequence
<220> FEATURE:
<223> OTHER INFORMATION: Description of Combined DNA/RNA Molecule:
      Oligonucleotide
<223> OTHER INFORMATION: Description of Artificial Sequence: Novel
      Sequence

<400> SEQUENCE: 15
```

```
cgcagagagu aaacgc                                                    16
```

<210> SEQ ID NO 16
<211> LENGTH: 15
<212> TYPE: DNA
<213> ORGANISM: Artificial Sequence
<220> FEATURE:
<223> OTHER INFORMATION: Description of Combined DNA/RNA Molecule:
      Oligonucleotide
<223> OTHER INFORMATION: Description of Artificial Sequence: Novel
      Sequence

<400> SEQUENCE: 16

```
cgcagacagu aaacg                                                     15
```

<210> SEQ ID NO 17
<211> LENGTH: 16
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 17

```
cgcagacagc aaacgc                                                    16
```

<210> SEQ ID NO 18
<211> LENGTH: 16
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 18

```
cgcagaaagc aaacgc                                                    16
```

<210> SEQ ID NO 19
<211> LENGTH: 16
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 19

```
cgcagagagc aaacgc                                                    16
```

<210> SEQ ID NO 20
<211> LENGTH: 16
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 20

```
cgcagatagc aaacgc                                                    16
```

<210> SEQ ID NO 21
<211> LENGTH: 10
<212> TYPE: DNA
<213> ORGANISM: Artificial Sequence
<220> FEATURE:
<223> OTHER INFORMATION: Description of Artificial Sequence: Novel
      Sequence

```
<400> SEQUENCE: 21
agtgatctac                                                          10

<210> SEQ ID NO 22
<211> LENGTH: 10
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 22
agtgatctac                                                          10

<210> SEQ ID NO 23
<211> LENGTH: 10
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 23
gtagatcact                                                          10

<210> SEQ ID NO 24
<211> LENGTH: 10
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (6)
<223> OTHER INFORMATION: n is an incorporated N-(benzo [b] [1,8]
      napthyridin-2-(1H)-on-3-yl)
      acetyl)-N-(2-Boc-aminoethyl) glycine monomer.

<400> SEQUENCE: 24 gtagancact                                                          10

<210> SEQ ID NO 25
<211> LENGTH: 10
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (2)
<223> OTHER INFORMATION: n is an incorporated N-(benzo [b] [1,8]
      napthyridin-2-(1H)-on-3-yl)
      acetyl)-N-)2-Boc-aminoethyl) glycine monomer.
<221> NAME/KEY: misc_feature
<222> LOCATION: (6)
<223> OTHER INFORMATION: n is an incorporated N-(benzo [b] [1,8]
      napthyridin-2-(1H)-on-3-yl)
      acetyl)-N-(2-Boc-aminoethyl) glycine monomer.
<221> NAME/KEY: misc_feature
<222> LOCATION: (10)
<223> OTHER INFORMATION: n is an incorporated N-(benzo [b] [1,8]
      napthyridin-2(1H)-on-3-yl)
      acetyl)-N-(2-Boc-aminoethyl) glycine monomer.

<400> SEQUENCE: 25 gnagancacn                                                          10
```